United States Patent
Zou et al.

(10) Patent No.: US 11,229,419 B2
(45) Date of Patent: Jan. 25, 2022

(54) METHOD FOR PROCESSING 3D IMAGE DATA AND 3D ULTRASONIC IMAGING METHOD AND SYSTEM

(71) Applicant: SHENZHEN MINDRAY BIO-MEDICAL ELECTRONICS CO., LTD., Shenzhen (CN)

(72) Inventors: Yaoxian Zou, Shenzhen (CN); Kyle Brennan, Sammamish, WA (US); Muqing Lin, Shenzhen (CN); Zhijie Chen, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 444 days.

(21) Appl. No.: 15/678,985

(22) Filed: Aug. 16, 2017

(65) Prior Publication Data
US 2017/0367685 A1 Dec. 28, 2017

Related U.S. Application Data

(63) Continuation of application No. PCT/CN2015/073209, filed on Feb. 16, 2015.

(51) Int. Cl.
*A61B 8/08* (2006.01)
*G06T 7/73* (2017.01)
(Continued)

(52) U.S. Cl.
CPC .......... *A61B 8/5207* (2013.01); *A61B 8/0808* (2013.01); *A61B 8/0866* (2013.01);
(Continued)

(58) Field of Classification Search
CPC ......... A61B 8/5207; A61B 8/461; A61B 8/14; A61B 8/0866; A61B 8/0808; A61B 8/483;
(Continued)

(56) References Cited

U.S. PATENT DOCUMENTS 7,780,600 B2 * 8/2010 Krantz ................. G06T 7/0012
600/443
8,083,678 B2 12/2011 Abuhamad
(Continued)

FOREIGN PATENT DOCUMENTS

| CN | 1034855 A | 8/1989 |
|----|-----------|--------|
| CN | 101011266 | 8/2007 |

(Continued)

OTHER PUBLICATIONS

Dong Ni, et al.; Learning Based Automatic Head Detection and Measurement from Fetal Ultrasound Images via Prior Knowledge and Imaging Parameters; Apr. 7-11, 2013; 2013 IEEE 10th International Symposium on Biomedical Imaging: From Nano to Macro; San Francisco, CA, USA.

*Primary Examiner* — Amanda Lauritzen Moher
*Assistant Examiner* — Amy J Shafqat
(74) *Attorney, Agent, or Firm* — Kory D. Christensen

(57) ABSTRACT

A method for display processing of 3D image data includes obtaining 3D volume data of the head of a target body; detecting a transverse section at an anatomical position from the 3D volume data according to image characteristic of the head of the target body in a transverse section related to the anatomical position; and displaying the transverse section.

11 Claims, 15 Drawing Sheets

(51) Int. Cl.
*A61B 8/14* (2006.01)
*A61B 8/00* (2006.01)
*G06K 9/62* (2006.01)
*G06T 7/00* (2017.01)

(52) U.S. Cl.
CPC ............... *A61B 8/14* (2013.01); *A61B 8/461* (2013.01); *G06K 9/6215* (2013.01); *G06K 9/6256* (2013.01); *G06K 9/6267* (2013.01); *G06T 7/0014* (2013.01); *G06T 7/74* (2017.01); *A61B 8/483* (2013.01); *G06T 2200/04* (2013.01); *G06T 2207/10088* (2013.01); *G06T 2207/10136* (2013.01); *G06T 2207/30016* (2013.01); *G06T 2207/30044* (2013.01)

(58) Field of Classification Search
CPC ............ G06T 7/74; G06T 7/0014; G06T 2207/30044; G06T 2207/10088; G06T 2207/30016; G06T 2207/10136; G06T 2200/04; G06K 9/6267; G06K 9/6256; G06K 9/6215
See application file for complete search history.

(56) References Cited

U.S. PATENT DOCUMENTS

| | | | |
|---|---|---|---|
| 2005/0251036 A1* | 11/2005 | Abuhamad | A61B 8/08 600/437 |
| 2005/0251039 A1* | 11/2005 | Chalana | G06T 7/143 600/437 |
| 2005/0283078 A1 | 12/2005 | Steen | |
| 2006/0100512 A1 | 5/2006 | Lee | |
| 2007/0081705 A1 | 4/2007 | Carneiro et al. | |
| 2007/0110291 A1 | 5/2007 | Ahn et al. | |
| 2010/0080485 A1* | 4/2010 | Chen | G06T 5/003 382/266 |
| 2010/0217123 A1 | 8/2010 | Eran et al. | |
| 2011/0054324 A1 | 3/2011 | Lee | |
| 2011/0224546 A1* | 9/2011 | Lee | G06T 7/60 600/443 |
| 2014/0126790 A1* | 5/2014 | Duchesne | G06T 7/0002 382/128 |
| 2015/0250455 A1* | 9/2015 | Lee | G06T 7/73 382/131 |

FOREIGN PATENT DOCUMENTS

| | | |
|---|---|---|
| CN | 101238987 A | 8/2008 |
| CN | 101692286 A | 4/2010 |
| CN | 201516047 | 6/2010 |
| CN | 101791231 A | 8/2010 |
| CN | 102028498 A | 4/2011 |
| CN | 102688071 A | 9/2012 |
| CN | 102754125 A | 10/2012 |
| CN | 102805648 A | 12/2012 |
| CN | 103654851 A | 3/2014 |
| CN | 104414680 A | 3/2015 |
| CN | 106102585 A | 11/2016 |
| JP | 2011206281 A | 10/2011 |
| WO | WO2011039515 | 4/2011 |
| WO | WO 2012031556 A1 | 3/2012 |
| WO | WO 2013/095032 A1 | 6/2013 |

* cited by examiner

METHOD FOR PROCESSING 3D IMAGE DATA AND 3D ULTRASONIC IMAGING METHOD AND SYSTEM

CROSS-REFERENCE TO RELATED APPLICATIONS

This application is a continuation of PCT Application No. PCT/CN2015/073209, filed Feb. 16, 2015, for METHOD FOR PROCESSING 3D IMAGE DATA AND 3D ULTRASONIC IMAGING METHOD AND SYSTEM, with inventors Yaoxian Zou, Kyle Brennan, Muqing Lin, and Zhijie Chen, which application is incorporated herein by reference in its entirety.

TECHNICAL FIELD

The present disclosure relates to ultrasonic imaging.

SUMMARY

Methods and systems for processing 3D image data are disclosed.

DETAILED DESCRIPTION

Figure 1:
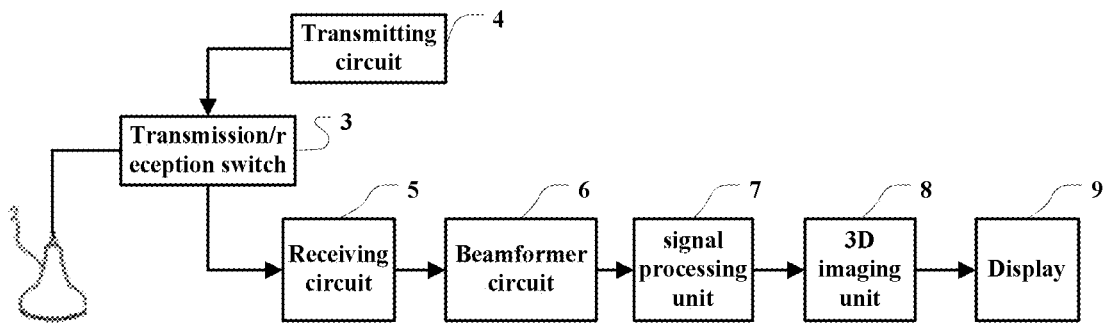
FIG. 1 is a block schematic diagram of a 3D ultrasonic imaging system according to one embodiment of the present disclosure.

Nuclear magnetic resonance detection instruments or ultrasonic instruments are generally used for clinical observation of the internal organization structure of human body. For example, when doctor puts an ultrasonic probe of an ultrasonic instrument on the surface of skin corresponding to certain body parts, ultrasound images of the parts can be obtained. Ultrasonic imaging, due to its safe, convenient, non-destructive and low-cost nature, has become one of the main auxiliary means of clinical diagnoses, and the maternity department is one of the diagnoses in which the ultrasonic imaging is most widely used. In this field, ultrasonic imaging equipment, without the side effect of X-ray, etc. to the mother and fetus, has better application value than other imaging equipment. Ultrasound can not only be used for morphological observation and measurement of the fetus, but also be used to obtain various physiological and pathological information such as fetal respiratory and urinary, thus to evaluate the fetus' health and development status. In the obstetric ultrasound examination, the most widely used techniques include gray-scale imaging, color flow imaging, pulse wave Doppler (PW) imaging and 3D/4D imaging.

In the ultrasonic diagnostic equipment, common standard sections which usually need to be displayed include fetal median sagittal section, cerebellum section, thalamus section, lateral ventricle section. In normal ultrasonic diagnostic equipment, due to positions of the fetus, sound shadow, or doctor's skill, etc., some standard section is hard to be obtained (for example, the fetal median sagittal section). Doctors usually need to frequently change the position of probe to look for the standard section, sometimes even ask pregnant women get off the examination bed and walk around to change the position of the fetus. Furthermore, if the position is not correctly localized, doctors can't obtain precise image data for displaying. Therefore, this kind of operation is not easy, and has high requirements to the operator. Non-standardly located section will eventually affect the accuracy of the image of the ultrasonic diagnostic equipment. As a result, it can't provide precise data for reference to practitioners. Moreover, the normal ultrasonic diagnosis need to take a very long time to obtain the above mentioned four sections and thus have low efficiency.

It is easy to understand that, on one hand, the existing ultrasonic diagnostic equipment take a long time to acquire accurate section images, and on the other hand, repeated operations on keys would cause strain of the doctor's body, which may cause occupational disease after long time of work. In recent years, with the wide application of 3D ultrasound imaging in clinical, resolution of the 3D ultrasound image is becoming higher and higher. In theory, the volume data acquired by the 3D ultrasound imaging will include all the standard sections of a structure inspected by doctors. However, the doctors need to manually process the volume data, by rotation, translation and other geometric transformation, to obtain desired standard sections in the 3D volume data and perform corresponding measurements on the standard sections, which will have high requirements for operators. The operators need to have not only 3D space imagination ability, but also certain understanding of medical anatomy knowledge, which is not easy. Furthermore, it, even if possible, will take a long time to obtain the desired sections from the volume data through manual adjustment, which means the efficiency is low. In addition, due to difference between operators, standard level of the sections obtained through manual operations may vary and cannot be consolidated, which may led to downfall of precision of section image obtained by the ultrasonic diagnostic equipment. Therefore the user's needs may not be fulfilled, and the equipment's application effect drops down, thus the equipment may not be widely used or popular in families.

Similarly, in other instrument that can obtain 3D image data of inspected body such as nuclear magnetic resonance, etc., there exists the same problem as that in the aforementioned ultrasonic instrument, i.e. the position of the standard section cannot be accurately and efficiently obtained from the 3D image data. Therefore, further improvement of the existing medical imaging data display processing technology is required.

In one embodiment, a method for processing 3D image data is provided. The method may include obtaining 3D volume data of a head of a target body, obtaining a transverse section image at an anatomical position of the head from the 3D volume data according to image characteristic of a transverse section of the head of the target body at the anatomical position, and displaying the transverse section image.

In one embodiment, the image characteristic may be image grayscale characteristic.

In one embodiment, obtaining the transverse section image at the anatomical position from the 3D volume data according to the image characteristic of the transverse section of the head of the target body at the anatomical position may include extracting a candidate transverse section image set from the 3D volume data, obtaining a transverse section template image generated according to collected images at the anatomical position of at least one sample body, calculating a similarity index between each candidate transverse section image of the candidate transverse section image set and the transverse section template image to obtain a set of similarity indexes, selecting a similarity index which satisfies an image characteristic condition from the set of similarity indexes, and obtaining the candidate transverse section image corresponding to the selected similarity index as the transverse section image.

In one embodiment, obtaining the transverse section image at the anatomical position from the 3D volume data according to image characteristic of the transverse section of the head of the target body at the anatomical position may include obtaining a median sagittal section image of the head from the 3D volume data, and obtaining the transverse section image from the 3D volume data based on the median sagittal section image.

In one embodiment, obtaining the transverse section image based on the median sagittal section image may include extracting candidate transverse section image set from the 3D volume data based on the median sagittal section image, obtaining a transverse section template image generated according to collected images at the anatomical position of at least one sample body, calculating a similarity index between each candidate transverse section image of the candidate transverse section image set and the transverse section template image to obtain a set of similarity indexes, selecting a similarity index which satisfies an image characteristic condition from the set of similarity indexes, and obtaining a candidate transverse section image corresponding to the selected similarity index as the transverse section image.

In one embodiment, extracting candidate transverse section image set from the 3D volume data based on the median sagittal section image may include extracting a reference target area from the median sagittal section image, and extracting transverse section images which are perpendicular to the median sagittal section image and pass through the reference target area to form the candidate transverse section image set, or, extracting a 3D volume data part containing the reference target area from the 3D volume data based on the transverse section images perpendicular to the median sagittal section image to obtain the candidate transverse section image set.

In one embodiment, calculating the similarity index between each candidate transverse section image of the candidate transverse section image set and the transverse section template image to obtain the set of similarity indexes may include extracting image characteristic from the transverse section template image to obtain a first characteristic quantity, respectively extracting an image characteristic from each candidate transverse section image of the candidate transverse section image set as a second characteristic to obtain a set of second characteristic quantities, and respectively calculating a likelihood between each second characteristic quantity of the set of second characteristic quantities and the first characteristic quantity to obtain the set of similarity indexes.

In one embodiment, calculating a similarity index between each candidate transverse section image of the candidate transverse section image set and the transverse section template image to obtain a set of similarity indexes may include constructing an image classification model, and training the image classification model by utilizing the transverse section template image to obtain a trained image classification model, and respectively inputting each candidate transverse section image of the candidate transverse section image set to the trained image classification model to obtain a classification tag corresponding to each candidate transverse section image to obtain the set of similarity indexes.

In one embodiment, extracting the candidate transverse section image set from the 3D volume data based on the median sagittal section image may include: extracting a straight line in a preset interval or extracting a straight line passing through a specific target area based on a linear equation on the median sagittal section image and obtaining from the 3D volume data a transverse section image which contains the straight line and is perpendicular to the median sagittal section image to construct the candidate transverse section image set; or, extracting a tangent on a boundary of a specific target area based on a linear equation on the median sagittal section image and obtaining a 3D volume data part containing the specific target area from the 3D volume data by utilizing a transverse section image which contains the tangent and is perpendicular to the median sagittal section image to obtain the transverse candidate section image set.

In one embodiment, prior to calculating the similarity index between each candidate transverse section image of the candidate transverse section image set and the transverse section template image, the method may further include adjusting the candidate transverse section image set and/or the transverse section template image such that the candidate transverse section image set and the transverse section template image have a same scale.

In one embodiment, adjusting the candidate transverse section image set and/or the transverse section template image such that the candidate transverse section image set and the transverse section template image have a same scale may include detecting an object of interest of the candidate transverse section image of the candidate transverse section image set, and adjusting the candidate transverse section image set to the same scale with the transverse section template image according to a size of the object of interest.

In one embodiment, a method for 3D ultrasonic imaging is provided. The method may include transmitting ultrasound waves to a head of a target body, receiving ultrasonic echoes to obtain ultrasonic echo signals, obtaining 3D volume data of the head of the target body based on the ultrasonic echo signals, obtaining a transverse section image at an anatomical position of the head from the 3D volume data according to image characteristic of a transverse section of the head of the target body at the anatomical position, and displaying the transverse section image.

In one embodiment, the image characteristic may be image grayscale characteristic of image.

In one embodiment, obtaining the transverse section image at the anatomical position from the 3D volume data according to the image characteristic of the transverse section of the head of the target body at the anatomical position may include extracting candidate transverse section image set from the 3D volume data, obtaining a transverse section template image generated according to collected images at the anatomical position of at least one sample body, calculating a similarity index between each candidate transverse section image of the candidate transverse section image set and the transverse section template image to obtain a set of similarity indexes, selecting a similarity index which satisfies an image characteristic condition from the set of similarity indexes, and obtaining the candidate transverse section image corresponding to the selected similarity index as the transverse section.

In one embodiment, obtaining the transverse section image at the anatomical position from the 3D volume data according to the image characteristic of the transverse section of the head of the target body at the anatomical position may include obtaining a median sagittal section image of the head from the 3D volume data, and obtaining the transverse section image from the 3D volume data based on the median sagittal section image.

In one embodiment, obtaining the transverse section image from the 3D volume data based on the median sagittal section image may include extracting candidate transverse section image set from the 3D volume data based on the median sagittal section image, obtaining a transverse section template image generated according to collected images at the anatomical position of at least one sample body, calculating a similarity index between each candidate transverse section image of the candidate transverse section image set and the transverse section template image to obtain a set of similarity indexes, selecting a similarity index which satisfies an image characteristic condition from the set of similarity indexes, and obtaining a candidate transverse section image corresponding to the selected similarity index as the transverse section image.

In one embodiment, extracting the candidate transverse section image set from the 3D volume data based on the median sagittal section image may include extracting a reference target area from the median sagittal section image, and extracting transverse section images which are perpendicular to the median sagittal section image and pass through the reference target area to obtain the candidate transverse section image set, or, extracting a 3D volume data part containing the reference target area from the 3D volume data based on the transverse section images perpendicular to the median sagittal section to obtain the candidate transverse section image set.

In one embodiment, calculating the similarity index between each candidate transverse section image of the candidate transverse section image set and the transverse section template image to obtain the set of similarity indexes may include extracting image characteristic from the transverse section template image to obtain a first characteristic quantity, respectively extracting an image characteristic from each candidate transverse section image of the candidate transverse section image set as a second characteristic to obtain a set of second characteristic quantities, and respectively calculating a likelihood between each second characteristic quantity of the set of second characteristic quantities and the first characteristic quantity to obtain the set of similarity indexes.

In one embodiment, calculating the similarity index between each candidate transverse section image of the candidate transverse section image set and the transverse section template image to obtain the set of similarity indexes may include constructing an image classification model, and training the image classification model by utilizing the transverse section template image to obtain a trained image classification model, and respectively inputting each candidate transverse section image of the candidate transverse section image set to the trained image classification model to obtain a classification tag corresponding to each candidate transverse section image to obtain the set of similarity indexes.

In one embodiment, extracting the candidate transverse section image set from the 3D volume data based on the median sagittal section image may include: extracting a straight line in a preset interval or extracting a straight line passing through a specific target area based on a linear equation on the median sagittal section image and obtaining from the 3D volume data a transverse section image which contains the straight line and is perpendicular to the median sagittal section image to construct the candidate transverse section image set; or, extracting a tangent on a boundary of a specific target area based on a linear equations on the median sagittal section image and obtaining a 3D volume data part containing the specific target area from the 3D volume data by utilizing a transverse section image which contains the tangent and is perpendicular to the median sagittal section image to obtain the transverse candidate section image set.

In one embodiment, a 3D ultrasonic imaging system may be provided. The system may include a probe which transmits ultrasound to and receives ultrasound echoes from a head of a target body to obtain ultrasound echo signals; a 3D imaging unit which obtains 3D volume data based on the ultrasound echo signals, and obtain a transverse section image at an anatomical position of the head from the 3D volume data according to image characteristic of a transverse section of the head of the target body at the anatomical position; and a display which displays the transverse section image.

In one embodiment, a method for processing 3D image data is provided. The method may include obtaining 3D volume data of a head of a target body, obtaining a section image at an anatomical position from the 3D volume data according to image characteristic of a section of the head of the target body at the anatomical position, generating an indicator indicating the anatomical position of the obtained section image, and displaying the obtained section image and the indicator.

In one embodiment, the indicator may be an intersection line of the section image and a reference image.

In one embodiment, the indicator may be displayed on a section schematic.

In one embodiment, the indicator may be displayed on at least one of a sagittal section image, a coronal section image and a transverse section image of the 3D volume data.

In one embodiment, the obtained section image may be a median sagittal section image, and the indicator may be displayed on the median sagittal section image.

In one embodiment, the indicator may be displayed on a section schematic of a median sagittal section image.

In one embodiment, the indicator may be an intersection line of the transverse section and the median sagittal section image.

In one embodiment, the method may further include receiving a signal generated by a user selecting the indicator or at least a section image and converting the selected indicator or the indicator of the selected section image from visible to invisible or from invisible to visible.

In one embodiment, the method may further include receiving an adjustment instruction in respect of the anatomical position, obtaining a section image at the adjusted anatomical position according to the adjustment instruction, and displaying the section image at the adjusted anatomical position.

In one embodiment, the method may further include acquiring an initial position and a terminal position marked on the reference image; and playing in sequence a plurality of parallel section images between the initial position and the terminal position, or, comparatively displaying a plurality of parallel section images between the initial position and the terminal position.

In one embodiment, a 3D ultrasonic imaging system is provided. The system may include a probe which transmits ultrasound waves to and receives ultrasound echoes from a head of a target body to obtain ultrasound echo signals; a 3D imaging unit which obtains 3D volume data of the head of the target body according to the ultrasound echo signals, obtains a section image at an anatomical position from the 3D volume data according to image characteristic of a section of the head of the target body at the anatomical position, and generates an indicator indicating the anatomical position of the obtained section image; and a display which displays the obtained section image and the indicator.

In one embodiment, a method for processing 3D image data is provided. The method may include obtaining 3D volume data of a head of a target body, obtaining a section image at an anatomical position from the 3D volume data according to image characteristic of a section of the head of the target body at the anatomical position, detecting an object of interest in the section image, automatically measuring a parameter of the object of interest, and displaying an indicator of the object of interest and/or the measured parameters of the object of interest.

In one embodiment, detecting the object of interest in the section image may include fitting a region of interest in the section image using a model which matches the object of interest to obtain the object of interest.

In one embodiment, the section image may include a transverse section image, and detecting the object of interest in the section image may include fitting a region of interest detected from the transverse section image using an ellipse model to obtain a biggest ellipse as the object of interest.

In one embodiment, automatically measuring the parameter of the object of interest may include: automatically measuring a circumference of the ellipse; and/or automatically measuring a short axis of the ellipse or a distance between two nearby points of two ends of the short axis; and/or automatically measuring a long axis of the ellipse or a distance between two nearby points of two ends of the long axis.

In one embodiment, the nearby points may be the points near two ends of the short axis or the long axis and with brightness decreasing most drastically along direction of the short axis or the long axis.

In one embodiment, automatically measuring the parameter of the object of interest may include: searching, starting from an arbitrary point on a long axis of the ellipse, a point or region with gray scale which decrease most drastically as a first point; searching, starting from the first point, a point or region with gray scale which increase most drastically as a second point; and measuring a distance between the first point and the second point.

In one embodiment, detecting the object of interest in the section image and automatically measuring the parameter of the object of interest may include: detecting a boundary of the object of interest according to characteristic of the object of interest in a searching region set in the ellipse or in the ellipse to obtain a region of the object of interest; and measuring a distance between two points with maximum vertical distance in the region.

In one embodiment, the section image may be a median sagittal section image, and detecting the object of interest in the section image may include: designating a searching scope for cauda cerebelli in a median sagittal section image based on an anatomical position of a section of a cerebellum in a median sagittal section and a transverse diameter of the cerebellum; and segmenting a region of the cauda cerebella in the searching scope as the object of interest.

In one embodiment, automatically measuring the parameter of the object of interest may include: searching two points having maximum horizontal distance and two points having maximum vertical distance in the region of the cauda cerebelli and measuring a horizontal distance between the two points having maximum horizontal distance and a vertical distance between the two points having maximum vertical distance, respectively; or, fitting the region of the cauda cerebella using an ellipse model to obtain a fitted ellipse and measuring length of a long axis and a short axis of the fitted ellipse.

In one embodiment, the section image may be a median sagittal section image and/or a transverse section image, and detecting the object of interest in the section image may include detecting the object of interest in the median sagittal section image and/or the transverse section image, wherein the transverse section image comprises at least one of thalamus section image, cerebellum section image and lateral ventricles section image.

In one embodiment, a 3D ultrasonic imaging system is provided. The system may include: a probe which transmits ultrasound waves to and receives ultrasound echoes from a head of a target body to obtain ultrasound echo signals; a 3D imaging unit which obtains 3D volume data of the head of the target body according to the ultrasound echo signals, obtain a section image at an anatomical position from the 3D volume data according to image characteristic of a section of the head of the target body at the anatomical position, detects an object of interest in the section image and automatically measures a parameter of the object of interest; and a display which displays an indicator of the object of interest and/or the measured parameters of the object of interest.

Based on display processing technology for medical 3D image data in the related arts, the present disclosure provides a method and system which may automatically identify a standard transverse section image of the head of a target body from the 3D image data by utilizing the image identify technology, therefore enhance the precision and the high efficiency of obtaining transverse section image at anatomical positions from the 3D image data. The details of the embodiments of the present disclosure will be described incorporated by the attached drawings hereinafter. The followings will describe obtain manners of the 3D volume data in details by taking a 3D ultrasonic imaging system for example.

As shown in FIG. 1, it is a block schematic diagram of the 3D ultrasonic imaging system. The 3D ultrasonic imaging system includes a probe 2, a transmission/reception switch 3, a transmitting circuit 4, a receiving circuit 5, a beamformer unit 6, a signal processing unit 7, a 3D imaging unit 8, and a display 9. The transmitting circuit 4 transmit a set of delay focused pulses to the probe 2, the probe 2 emit ultrasound to the target body's tissue (not shown in the figures), receive ultrasound echoes containing tissue information reflected by the target body's tissue after certain delay, and re-transform the ultrasound echoes to electrical signals. The receiving circuit 5 receives the electrical signal and sends these ultrasound echo signals to the beamformer unit 6. The ultrasound echo signals are processed in the beamformer unit 6 to complete the focusing delay, weighting and channel accumulation, and processed by the signal processing unit. The signals processed by the signal processing unit 7 are sent to the 3D imaging unit 8 to be processed to obtain visualized information such as 3D images, after that, the visualized information is sent to the display 9 for displaying.

When the probe 2 finished one scan period of scanning, the signals processed by the signal processing unit 7 form a volume of 3D volume data in Polar coordinates in the 3D imaging unit 8, the 3D volume data in Polar coordinates are transformed to volume data in Cartesian coordinates after reconstruction processing, thus to obtain a volume of 3D volume data in Cartesian coordinates. After that, the 3D imaging unit 8 perform calculation to the 3D volume data in Cartesian coordinates by using a visualization algorithm, to obtain visualized information for displaying on display equipment.

In some embodiments of the present disclosure, the 3D imaging unit 8 of the 3D ultrasonic imaging system may further include a sub-unit for automatically detecting transverse section image of the head of the target body. The sub-unit may detect and display the transverse section image from the 3D volume data, according to image characteristic of the head of the target body in a transverse section image related to the anatomical position (will be described in details below). In the present disclosure, the mentioned head of a target body includes fetus head, head of human and head of animal. The anatomical position refers to the sectioning position obtaining corresponding transverse section image in the head of the head of the target body.

Similarly, one embodiment of the present disclosure provides a NMR imaging system which includes: a magnetic field control device for generating main magnetic field and gradient magnetic field, a radio-frequency transceiver for applying radio-frequency pulse signals and receiving FID signals, a signal detection unit and an image reconstruction unit.

The signal detection unit is configured to convert the received FID signals from analog signals to digital signals through an A/D converter, then to pre-process the converted signals appropriately by filtering and amplifying, etc. The signals processed by the signal detection unit are processed by the computer to obtain slice image data and then form the 3D volume data in the image reconstruction unit, according to corresponding relationship between the signals and volume pixels in a plane of view. The image reconstruction unit may calculate to obtain visualized information by using visualization algorithm. The visualized information may be displayed on the display equipment, and a slice image to be viewed may be displayed by using different gray scales according to amount of the nuclear magnetic resonance. The acquisition of the 3D volume data in the NMR imaging system can be referred to 3D stereoscopic contrast imaging technology in the NMR imaging, and will not be described in more details hereinafter. In another embodiment of the present disclosure, the image reconstruction unit in the NMR imaging system may further includes a sub-unit for automatically detecting transverse section image of the head of the target body, and the sub-unit may detect and display the transverse section from the 3D volume data, according to image characteristic of the head of the target body in a transverse section related to the anatomical position (will be described in details below).

Figure 2:
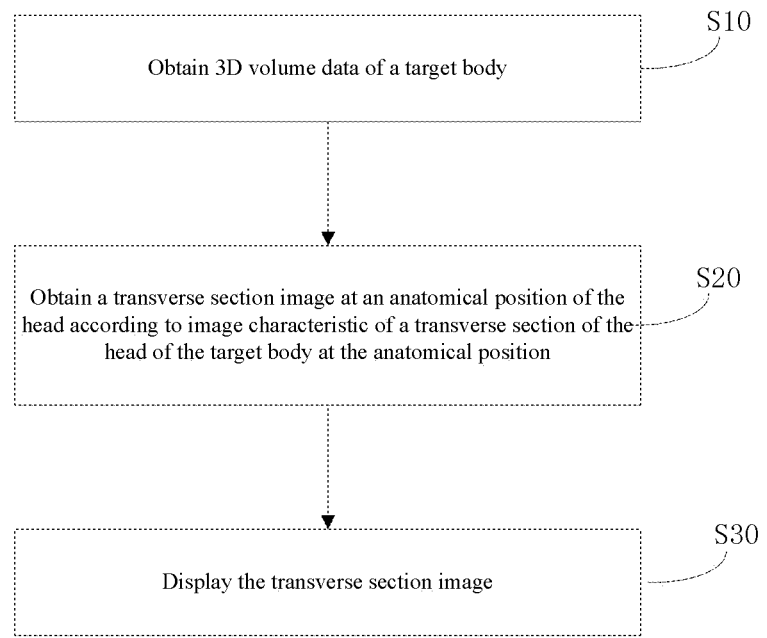
FIG. 2 is a schematic flow chart of a method according to one embodiment of the present disclosure.

As shown in FIG. 2, based on aforementioned the 3D volume data obtained by the NMR imaging system or the 3D ultrasonic imaging system, that is, image data which may be used to realize 3D stereoscopic imaging and displaying, one embodiment of the present disclosure provides a method of display processing for 3D image data.

In one embodiment of the present disclosure, the step S10 includes obtaining 3D volume data of the head of a target body. The 3D volume data includes the aforementioned 3D volume data obtained by the NMR imaging system or the 3D ultrasonic imaging system. Take the 3D volume data obtained by the ultrasonic imaging system as an example. Firstly, using the 3D ultrasonic imaging system to perform 3D scanning to the head of the target body such as a fetus head, emit ultrasound to the head of the target body and receive ultrasound echoes to obtain ultrasound echo signals. The ultrasound echo signals are processed according to aforementioned processing to obtain the 3D volume data of the head of the target body (hereinafter refers to the 3D volume data). The detailed steps of performing 3D canning to a scan target and processing the ultrasound echo signals to obtain 3D volume data may similar or identical to frequently-used 3D scanning and imaging methods in the arts, and will not be described in details herein.

After the step S10, at least a volume of 3D volume data of the target body (for example, the fetus head) may be obtained.

Figure 3:
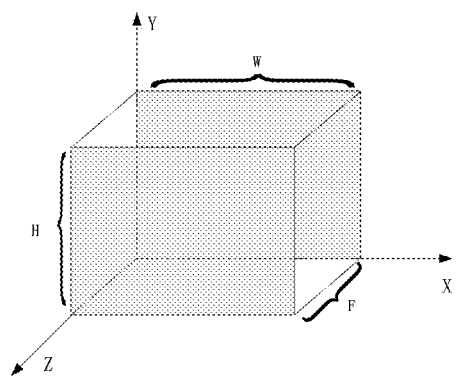
FIG. 3 is a schematic diagram of the 3D volume data according to one embodiment of the present disclosure.

For example, a schematic diagram of a volume of 3D volume data may be as shown in FIG. 3. It is can be seen in the FIG. 3 that the volume of 3D may be constructed by F frames of image frame with a size of W×H, wherein W is the width of the image frame, and H is the height of the image frame. In addition, it is also can be seen in the FIG. 3 that the width direction of the image frame is defined as X direction, the height direction of the image frame is defined as Y direction, and the direction along which a plurality of image frames are arranged is defined as Z direction. It should be understood that, the directions X, Y and Z may be defined according to different manners.

After the 3D volume data are obtained in the step S10, in a method of the present disclosure, it may desired to automatically detect a transverse section of the target body at a corresponding anatomical position from the 3D volume data, for example, one or more of a plurality of standard transverse sections including the cerebellum section, the thalamus section and the lateral ventricle section. The standard transverse sections have correct anatomical position, and correctly characterize of target tissues of the brain as many as possible, thus can provide the doctor good image information and analysis data. Medically, in order to reduce the number of sections, the observation vision of a plurality of target tissues as many as possible is desired to shown in one section. Therefore, the observation vision of more than one target tissue is usually shown in a standard transverse section. In the system according to the present disclosure, the user may select a target tissue to be observed (including various kinds of the brain tissue structures, such as cerebellum, thalamus, lateral ventricle, callosum, cauda cerebelli, cavum septi pellucidi, cerebellum cerebellomedullary cistern, interthalamic adhesion, and the fourth cerebral ventricle) to determine a needed anatomical position, thus to determine which one of the standard transverse sections to be detected. Or the system may show three standard transverse sections including the cerebellum section, the thalamus section and the lateral ventricle section by default; or the standard transverse sections needs to be detected is determined according to the anatomical position selected by the user, or the standard transverse sections needs to be detected may be determined directly by inputting the name of the standard transverse section. Certainly, the anatomy names of the aforementioned standard transverse sections are based on cognition of human brain anatomy, if the target body is replaced with other animal body, the aforementioned standard transverse section should be replaced with those based on cognition of corresponding animal brain anatomy, such as horizontal sections for dog's brain and cat's brain. The following will take the human fetus as the target body, to exemplarily illustrate the positions of the plurality of standard transverse sections for human brain.

Figure 4:
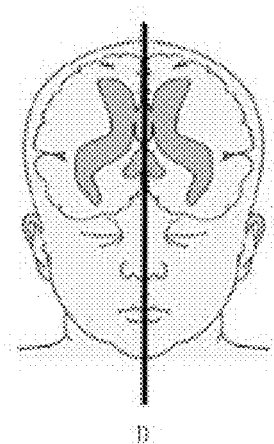
FIG. 4 is a schematic diagram of the location of median sagittal section image of a fetal brain.
Figure 5:
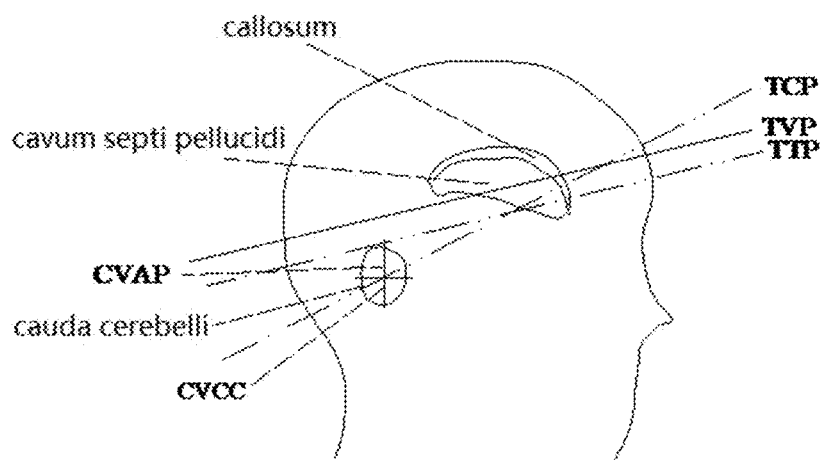
FIG. 5 is a schematic diagram of the median sagittal section image of the fetal brain.

If the target body is the fetus, the median sagittal section image position of the fetus may be as shown in FIG. 4. The line D in the FIG. 4 represents the median sagittal section image position of the fetal brain. A schematic diagram of the median sagittal section image of the fetal brain may be displayed in FIG. 5. It can be seen that, the median sagittal section image contains important information relating to target tissues such as callosum, cauda cerebelli, and cavum septi pellucid of the fetus. In addition, target tissue structure such as the cerebellum cerebellomedullary cistern, the interthalamic adhesion, and the fourth cerebral ventricle are also can be observed on the median sagittal section image of the fetal brain. Based on schematic diagram of the median sagittal section images as shown in FIG. 5, the correct anatomical position of the aforementioned plurality of standard transverse sections are also displayed in the figure, wherein the three standard transverse sections including the cerebellum section, the thalamus section and the lateral ventricle section are vertical to the median sagittal section respectively. The TCP represented by the double dot dash line in FIG. 5 marks the correct anatomical position of the cerebellum section (the double dot dash line refers to the vertical intersection line between the TCP section and the median sagittal section hereinafter). The brain midline, the cavum septi pellucidi, the cerebellum and the joint of the upper cerebellum and the lower cerebellum (that is, the cauda cerebella) can be seen in the cerebellum section. The TTP represented by the single dot dash line in FIG. 5 marks the correct anatomical position of the thalamus section (the single dot dash line refers to the vertical intersection line between the TTP section and the median sagittal section hereinafter). The structure of the thalamus, the brain midline and the cavum septi pellucid can be seen in the thalamus section. The TVP represented by the solid line marks the correct anatomical position of the lateral ventricle section (the solid line refers to the vertical intersection line between the TVP section and the median sagittal section hereinafter), the structure of the lateral ventricle and the cavum septi pellucidi may be seen in the section. Therefore, automatically detecting and displaying standard transverse section of the fetal brain or human brain may provide the practitioner a great amount of important key information, thus greatly facilitate the observation to fetus status for the practitioner. Certainly, according to medical development, the practitioner may need more brain transverse sections for observation, so the present disclosure should not be restricted to aforementioned three standard transverse sections. In the present disclosure, the detected transverse sections corresponding to the anatomical positions from the 3D volume data (hereinafter refers to the transverse section to be detected) may include: any one or a plurality of standard transverse sections obtained at the correct anatomical positions. In view of the brain anatomy, the aforementioned standard transverse sections may be vertical to any one of the brain sagittal section and/or the coronal section, for example, the three standard transverse sections including the cerebellum section, the thalamus section and the lateral ventricle section are all vertical to the brain median sagittal section image.

In the step S20 as shown in FIG. 2, detecting a transverse section at an anatomical position from the 3D volume data according to image characteristic of the head of the target body in a transverse section related to the anatomical position.

In the embodiments of the present disclosure, the image characteristic may include one or more of color characteristic, textural characteristic, shape characteristic, spatial relationship characteristic and projection characteristic of the image. The color characteristic refers to a global characteristic which describes the surface property of a subject corresponding to the image or image region. For example, it may be measured by characteristic quantities such as color histogram, color set, or color matrix. But different from the color characteristic, the textural characteristic is not based on pixel characteristic, it needs to statistically calculate in the region containing a plurality of pixels, for example, it may extract the textural characteristic by gray scale co-occurrence matrix analyzing, extract the textural characteristic from the self-correlation function of the image (that is, the energy spectrum function of the image), or extract the textural characteristic based on radon field model. The shape characteristic refers to characteristic detected or extracted by fitting based on shape of the target region of interest, for example, shape characteristic extracted based on Hough transformation detecting method and boundary direction histogram method. The Hough transformation is a method of connecting boundary pixels to constitute a regional enclosed boundary by utilizing image global characteristics. The boundary direction histogram method firstly calculates image boundary by utilizing differential image, then makes a histogram relates to boundary size and direction, for example, constructs a gradient direction matrix of image grayscale. The spatial relationship characteristic, which also can be regarded as the spatial relationship, refers to mutual spatial position or relative direction relationship between a plurality of targets segmented from the image. These relationships can be classified into two categories: connection/adjacent relationship, crossover/overlap relationship and containing/inclusive relationship, etc. Usually spatial position information may be classified into two categories: relative spatial position information and absolute spatial position information. The former relationship emphasizes on relative condition between the targets, such as relationship of up, down, left and right. The later relationship emphasizes on the distance and direction between the targets. For example, firstly based on skull halo and target region of interest segmented from the image, then take the location relationship between the target regions of interest of interest or the relative location relationship between the target region of interest and each point of the skull halo as the spatial relationship characteristic. The projection characteristic may be a projected value according to calculating/defining a projection transformation to project an image to a space corresponding to the transformation. For example, defines or calculates a matrix H, and multiplies the image and the transformation matrix H, then to obtain the image projection characteristic. Therefore, in one embodiment of the present disclosure, in the aforementioned step S20, detecting a transverse section from the 3D volume data according to image gray scale characteristic of the head of the target body in a transverse section related to the anatomical position. The image gray scale characteristic in the present disclosure may include characteristic for measuring texture variation of the gray scale image. It may also include gray scale characteristic expression obtained by utilizing convolution algorithm or spatial domain projection method to perform deformation or transformation to gray scale of the initial image, for example, gray scale value, gray scale gradient variation, image gray scale gradient direction matrix, gray scale statistical characteristic (such as projection characteristic of the image gray scale).

In addition, the method for detecting a transverse section at an anatomical position from the 3D volume data according to image characteristic of the head of the target body in a transverse section related to the anatomical position, is also detecting a transverse section with aforementioned image characteristic from the 3D volume date based on the image characteristic of the head of the target body in a transverse section related to the anatomical position. The above image characteristic of the transverse section related to the anatomical position may include: image characteristic of standard transverse sections such as cerebellum section, thalamus section and lateral ventricle section. For example, in aforementioned step S20, a transverse section may be detected (such as the cerebellum section) from aforementioned 3D volume data according to the image characteristic (such as the image characteristic of the cerebellum section) of the head of the target body in a transverse section related to an anatomical position; or, a plurality of transverse sections (such as standard transverse sections of cerebellum section, thalamus section and lateral ventricle section) may be detected from the 3D volume data according to the image characteristic (such as standard transverse section image characteristic of cerebellum section, thalamus section and lateral ventricle section) of the head of the target body in a transverse section related to a plurality of anatomical positions. Thus, in one embodiment of the present disclosure, at least a transverse section may be detected at an anatomical position from the 3D volume data according to the image characteristic of the head of the target body in a transverse section related to at least an anatomical position.

The image characteristic may be extracted from the corresponding image of at least a standard transverse section (that is, the transverse section image obtained at the correct anatomical position, hereinafter referred to as standard transverse section image), and also may be extracted by combining with the corresponding image of at least a non-standard transverse section (that is the transverse section image obtained at the corresponding anatomical position deviating from the standard transverse section, hereinafter referred to as non-standard transverse section image). Thus, the transverse section related to the anatomical position at least includes: standard transverse section related to the anatomical position of at least a sample body, or further include at least a non-standard transverse section. The transverse section related to an anatomical position mentioned herein includes: at least a standard transverse section obtained at the same correct anatomical position of at least a sample body, or at least a standard transverse section as mentioned above and at least a non-standard transverse section obtained from at least a position deviated from aforementioned correct anatomical position of the at least a sample body. Aforementioned sample body may refer to the head of the same species with the target body, and a different sample body represents head of different species, hereinafter the same.

For example, when utilizing aforementioned step S20 to automatically detect the cerebellum section, the image characteristic of the cerebellum section can be extracted according to the standard transverse section image at the correct anatomical position of the cerebellum section, which can be represented by the double dot dash line in FIG. 5 of the sample body, or can be extracted according to the standard transverse section image at the correct anatomical position of the cerebellum section represented by the double dot dash line in FIG. 5 of the sample body and the non-standard transverse section image at the correct anatomical position represented by the double dot dash line in deviation FIG. 5.

In order to extract the corresponding image characteristic according to the head of the target body in a transverse section related to the anatomical position, in one embodiment of the present disclosure, it also includes:

Firstly, collecting aforementioned transverse section related to the anatomical position of at least a sample body in advance to form the transverse section template image, which at least includes: the standard transverse section image related to the anatomical position and collected from at least a sample body, or can also include: the non-standard transverse section image collected from at least a sample body.

After that, extracts the corresponding image characteristic from the transverse section template image. The transverse section template image can be stored in a storage device in advance and can be directly read and obtained through the storage device during the 3D imaging procedure according to one or more embodiments of the present disclosure; and also can be generated during 3D imaging procedure according to other embodiments of the present disclosure.

In order to detect at least a transverse section from the 3D volume data, a transverse section related to at least an anatomical position of at least a sample body needs to be collected in advance to form the transverse section template image. There is a standard transverse section image related to an anatomical position of a sample body. Thus, the transverse section template image formed may include: at least a standard transverse section image obtained at a correct anatomical position of at least a sample body, or the standard transverse section image as mentioned above and at least a non-standard transverse section image obtained from at least a position deviated from the correct anatomical position of the at least a sample body.

In order to facilitate extracting the corresponding transverse section at the corresponding anatomical position or image characteristic extracting of the transverse section template image, thus in one embodiment of the present disclosure, the anatomical position and the transverse section template image can be correlated, marked and stored, or the anatomical position, the transverse section template image, the transverse section indicator to be detected and/or standard transverse section image of the transverse section template image and the classification tag of the non-standard transverse section image can also be correlated, marked and stored, etc. so as to automatically obtain and use the transverse section template image according user's needs. For example, a plurality of standard transverse section images obtained at the same correct anatomical position of different sample bodies can be correlated, and the correct anatomical position can be correlated and marked with. Or, at least a standard transverse section image and at least a non-standard transverse section image obtained at the same anatomical position of different sample bodies can be correlated, and the anatomical position (including correct or deviated position) and/or the cerebellum section indicator can be correlated and marked with. Take cerebellum section as an example, all cerebellum section images extracted from different sample bodies are correlated and stored with the correct anatomical position of the cerebellum section and/or the cerebellum section indicator and unified as cerebellum section template image; or, at least a standard transverse section image and at least a non-standard transverse section image of the cerebellum section extracted from different sample bodies are also correlated and stored with the correct anatomical position of the cerebellum section and/or the cerebellum section indicator and unified as cerebellum section template image.

Thus, in another embodiment of the present disclosure, in aforementioned step S20, a transverse section with aforementioned image characteristic can be detected from the 3D volume data to be regarded as the transverse section to be detected, by utilizing the image characteristic extracted from the transverse section template image related to the anatomical position of the head of the target body. For example, through the standard transverse section template images of the cerebellum section template image, thalamus section template image and/or lateral ventricle section template image of the transverse section of the fetus' head, and extracting image characteristic from these template images to detect transverse section images with aforementioned image characteristic from the candidate transverse section image as aforementioned transverse sections to be detected.

According to different image characteristic extracting method, different classes of transverse section template images can be chosen. In addition, in one embodiment of the present disclosure, the image characteristic extracted from the transverse section template image related to the anatomical position of the head of the target body in step S20 may include:

Extracting aforementioned image characteristic by utilizing the standard transverse section image related to the anatomical position and collected from at least a sample body, or Extracting aforementioned image characteristic by utilizing aforementioned standard transverse section image and non-standard transverse section image related to the anatomical position and collected from at least a sample body.

Figure 6:
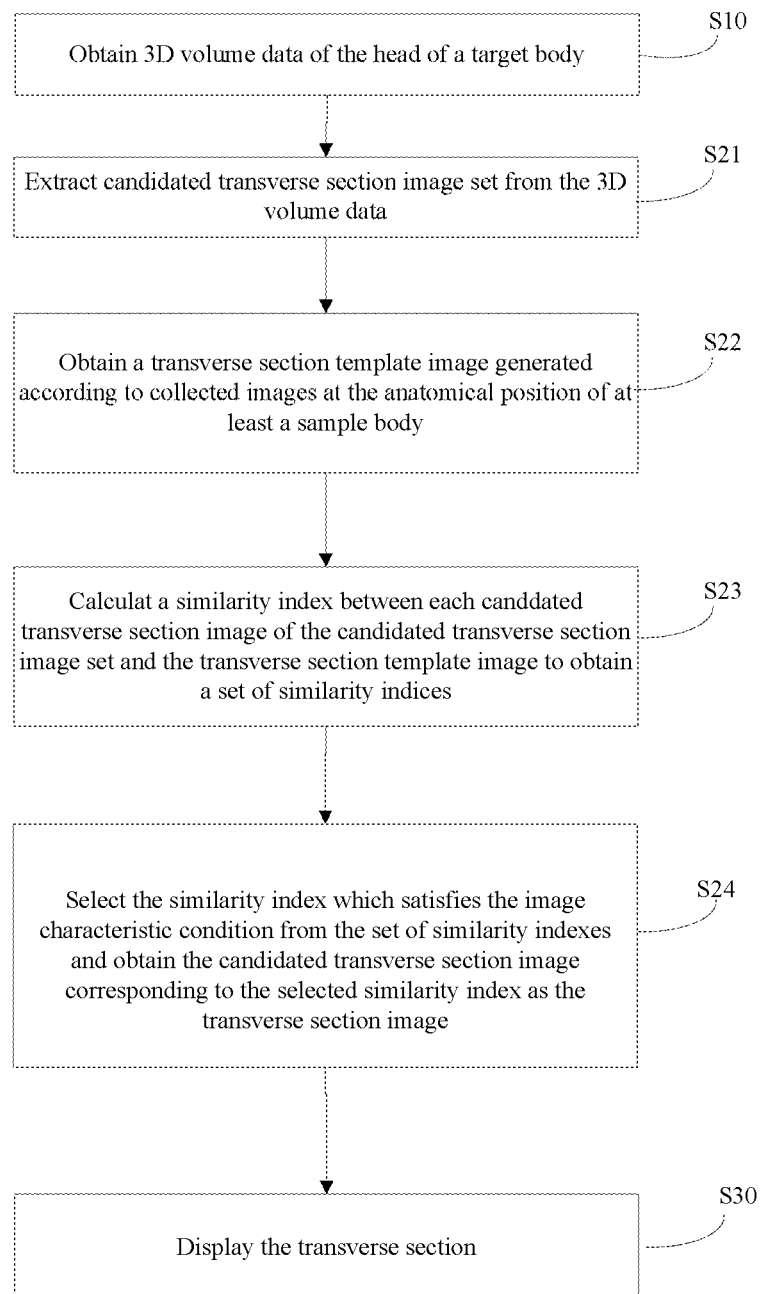
FIG. 6 is a schematic flow chart of a method according to one of the embodiments of the present disclosure.

Based on aforementioned transverse section template image, in one embodiment of the present disclosure as shown in FIG. 6, aforementioned step S20 may include the following steps of S21 and step S24.

In step S21 of embodiment of the present disclosure, extracting a candidate transverse section image set from the 3D volume data, the candidate transverse section image set may be the 2D image set containing at least one candidate transverse section image extracted from abovementioned 3D volume data, and it may also be part of the 3D volume data intercepted from the 3D volume data. Therefore, the method for extracting the candidate transverse section image from the candidate transverse section image set or the 3D volume data may refer to the following content.

The method for selecting the candidate transverse section image may be decided according to needs. For example, all the transverse sections apart at certain intervals (or step-length) at one or a plurality of specific directions within certain range of the 3D volume data may be selected. The certain range can be the angle range relative to one or a plurality of lines and/or planes of the 3D volume data, and can also be the distance range relative to one or a plurality of points, lines and/or planes of the 3D volume data; the at one or a plurality of directions refer to the normal of the section in one or the plurality of directions; the intervals or step-length may be distance intervals or step-length, and also may be angle intervals or step-length. The satisfying conditions of the selected candidate transverse section image also may be set, such as the selected candidate transverse section images can be all the sections perpendicular to an arbitrary brain sagittal section or coronal section.

In embodiment of the present disclosure, all the transverse sections apart at certain distance or step-length at one or a plurality of directions within all range of the 3D volume data can be selected; or, in embodiment of the present disclosure, the candidate transverse section image can be selected according to some prior knowledge and remove the images obviously not at the correct anatomical position, such as screening the candidate transverse section image (will be described in details hereinafter) by utilizing the detected median sagittal section.

Or, in embodiment of the present disclosure, the user input may also be received, and the user input can indicate the possible range where the transverse section needed may be located, and then the transverse section within the range indicated by the user can be selected as the candidate transverse section image.

In embodiment of the present disclosure, all the transverse sections apart at certain step-length of the 3D volume data can be selected, that is, to perform traversing searching to all the transverse sections within all range of the 3D volume data by certain step-length.

Based on this, in one embodiment of the present disclosure, in order to narrow down the range for detecting the transverse section of the 3D volume data, the steps for extracting candidate transverse section image set from the 3D volume data in step S21 may include:

Step S211, extracting a straight line at a preset interval or extracting a straight line passing through a specific target area based on a linear equation on an arbitrary brain sagittal section or coronal section of the 3D volume data; for example, an arbitrary brain sagittal section or coronal section can be a median sagittal section image, and the specific target area can be the region of interest such as the callosum, the cavum septi pellucidi, and the cauda cerebelli.

Step S212, obtaining from the 3D volume data the transverse sections which contain the straight line and are perpendicular to the arbitrary brain sagittal section or coronal section to construct the candidate transverse section image set.

Or it also can be, firstly, in aforementioned step S211, extracting tangent on the boundary of a specific target area, after that, in step S212, intercepting partial 3D volume data containing the specific target area from the 3D volume data by utilizing the transverse section containing the tangent and perpendicular to the arbitrary brain sagittal section or coronal section, to form the transverse candidate section image set. The tangent can be one line, or two, or more. In one embodiment of the present disclosure, intercepting partial 3D volume data containing the specific target area from the 3D volume data by utilizing the transverse section containing two tangents and perpendicular to the arbitrary brain sagittal section or coronal section. Furthermore, the two tangents may be parallel.

Transverse sections are all perpendicular to the brain sagittal section or coronal section, the projection of the transverse section on the sagittal section or coronal section is a straight line. Take the linear equation under polar coordinate system on the brain sagittal section as an example. The linear equation under polar coordinate system can be expressed by the equation as follows:

$$\rho = x \cos\theta + y \sin\theta \quad \text{Equation (1)}$$

$$-90° \leq \theta \leq 90° \quad \text{Equation (2)}$$

$$0 \leq \rho \leq \sqrt{w^2 + h^2} \quad \text{Equation (3)}$$

Wherein, w and h are the width and height of sagittal section image, $(\rho, \theta)$ can determine a straight line on the sagittal section, namely corresponding to a transverse section perpendicular to the sagittal section, and by sampling $(\rho, \theta)$ at certain interval, a plurality of candidate transverse section images can be determined to construct the candidate transverse section image set.

In specific embodiments, according to prior knowledge of application situation, locate the candidate transverse section image to a smaller search space to improve the speed and accuracy of subsequent detecting. The aforementioned three standard sections are all passing through the cavum septi pellucidi, thus, firstly detecting the location of the cavum septi pellucidi to narrow down the subsequent searching range. The cavum septi pellucidi presents low-echo with clear boundary which can be detected by normal threshold segmentation method, and after obtaining the location of the cavum septi pellucidi, candidate transverse section image can be selected among the transverse sections passing through the cavum septi pellucidi, thus narrow down the searching range of section to improve the speed and accuracy of automatic detecting.

Figure 7:
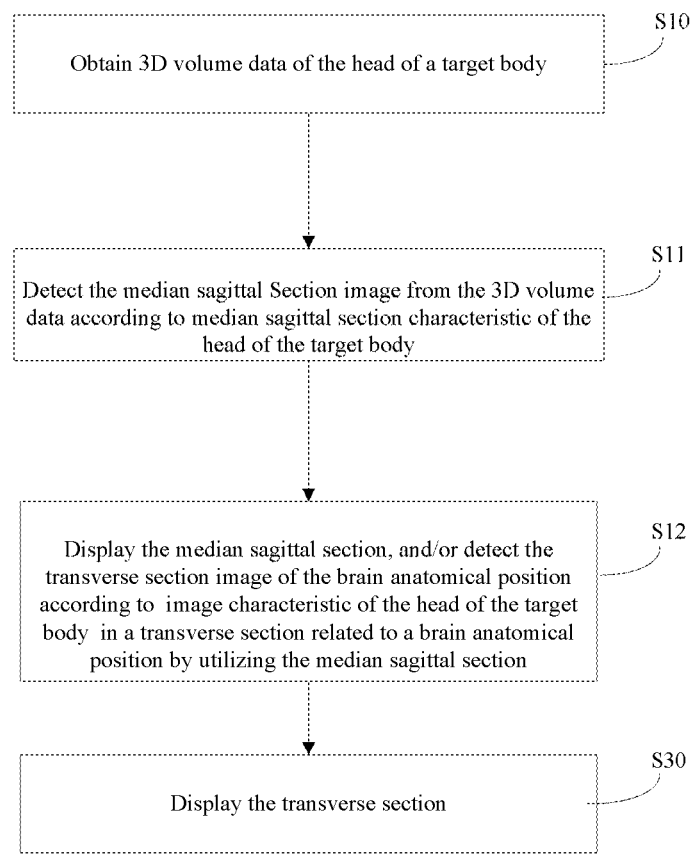
FIG. 7 is a schematic flow chart of a method according to one of the embodiments of the present disclosure.

Therefore, in one embodiment of the present disclosure as shown in FIG. 7, the method for display processing of 3D image data also includes:

Step S11, manually confirming the anatomical position of the median sagittal section image by the user to obtain the median sagittal section image from the 3D volume data. Or, detecting the median sagittal section image from the 3D volume data according to the characteristic of the median sagittal section image of the head of the target body. Automatic detecting method related to the median sagittal section image will be described in detail hereinafter.

Step S12, displaying the median sagittal section image, and/or utilizing the median sagittal section image to detect the transverse section at the anatomical position from the 3D volume date according to image characteristic of the head of the target body at the transverse section related to the anatomical position.

The main target tissues of the head may be observed by displaying the median sagittal section image in the embodiment to provide more comprehensive and accurate image data for the practitioner. In addition, the median sagittal section image obtained by detecting in the embodiment may be used to narrow down the detecting range related to the transverse section, namely alterations of step S21 are, utilizing the median sagittal section image to extract candidate transverse section image set (refer to previous text for definition related to candidate transverse section image set) from the 3D volume data. Specifically, in one embodiment of the present disclosure, the steps for utilizing the detected median sagittal section image to extract the candidate transverse section image set from the 3D volume data may include:

Firstly, segmenting the reference target area from the median sagittal section image. For example, the reference target area includes: region of interest of cavum septi pellucidi and so on, segmenting the region of interest of cavum septi pellucidi from the median sagittal section image through threshold segmentation method by utilizing the low-echo with clear boundary of the cavum septi pellucid, which may be shown in FIG. 5;

After that, extracting the transverse section perpendicular to the median sagittal section image and passing through a specific target area from the 3D volume data to construct the candidate transverse section image set. The extracting at present may also be extracting the transverse section perpendicular to the median sagittal section image and passing through a specific target area or the transverse section passing through a specific target area according to certain intervals to construct the candidate transverse section image set.

Figure 8:
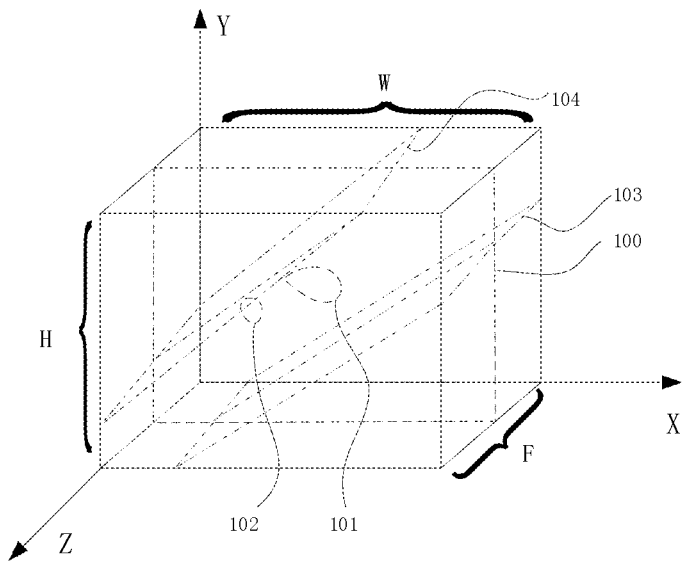
FIG. 8 is a schematic diagram of extracting candidate transverse section image set from the 3D volume data as shown in FIG. 3 according to one embodiment.

For example, as shown in FIG. 5, if it is to detect the three standard transverse sections of cerebellum section, thalamus section and lateral ventricle section, then extracting the transverse section perpendicular to the median sagittal section image and passing through region of interest of cavum septi pellucidi from the 3D volume data to construct the candidate transverse section image set for detecting the three standard transverse sections of cerebellum section, thalamus section and lateral ventricle section from the candidate transverse section image set. Or, as shown in FIG. 8, it may also be: intercepting the 3D volume data (namely the 3D volume data located between section 103 and 104 of the 3D volume data) containing reference target area (101 and/or 102) from the 3D volume data by utilizing the transverse section (section 104 constructed by single dot dash line and section 103 constructed by double dot dash line in FIG. 8) perpendicular to the median sagittal section image (section 100 constructed by dotted line in FIG. 8) of the 3D volume data to construct the candidate transverse section image set. In another embodiment of the present disclosure, it may also intercept the 3D volume data containing reference target area from the 3D volume data by utilizing the parallel transverse section perpendicular to the median sagittal section image to construct the candidate transverse section image set. The method for extracting the candidate transverse section image set from the intercepted 3D volume data can be realized by randomly extracting any quantity of transverse sections or according to aforementioned step S211 and step S212, or refer to other method related to extracting the candidate transverse section image set from the 3D volume data in previous text, which will not be described herein again.

When detecting the three standard transverse sections of cerebellum section, thalamus section and lateral ventricle section from the 3D volume data obtained in step S10, it may base on the same candidate transverse section image set, in other words, obtaining a candidate transverse section image set by executing aforementioned step 21 for only once and detecting the three standard transverse sections of cerebellum section, thalamus section and lateral ventricle section from the candidate transverse section image set. Similarly, when detecting a plurality of other standard transverse sections related to anatomical position, aforementioned step 21 can be executed repeatedly to obtain a plurality of different candidate transverse section image sets, of which, the corresponding reference target area or the specific target region shall be adjusted according to target tissues expected to be displayed by the standard transverse section, and similarly at least two standard transverse sections can be detected from a candidate transverse section image set, or a standard transverse section can also be detected from a candidate transverse section image set.

In one or more embodiments of the present disclosure, obtaining a transverse section template image generated according to collected images at a related brain structure position of at least a sample body in step S22. Obtainment of the transverse section template image can be seen from the above descriptions, which will not be described herein again.

In one or more embodiments of the present disclosure, calculating a similarity index between each candidate transverse section image of the candidate transverse section image set and the transverse section template image to obtain a set of similarity indexes in step S23. An arbitrary method can be adopted for extracting the candidate transverse section image from the candidate transverse section image set, for example, extracting any quantity (including all) of the candidate transverse section images according to a preset interval, or taking the candidate transverse section image set as the 3D volume data, for more detail please refer to aforesaid descriptions relating to the step S21.

The similarity index is used for measuring the similarity between the candidate transverse section image and the transverse section template image. In one or more embodiments of the present disclosure, the similarity index can be calculated in multiple ways.

For example, in one embodiment, the similarity index may be the sum of absolute value of difference of the gray scale value of the corresponding points of the candidate transverse section image and the transverse section template image, namely:

$$E = \sum_{I_L, I_R \in \Omega} |I_L - I_R|, \quad (4)$$

Wherein E is the similarity index, $\Omega$ is the image space of the candidate transverse section image, $I_L$ is the data value of the point of the candidate transverse section image, $I_R$ is the data value of the point of the transverse section template image corresponding to the point of the candidate transverse section image. Here, 'the corresponding points of the candidate transverse section image and transverse section template image' refer to the points with the identical position of the candidate transverse section image and the transverse section template image.

Or, in another embodiment of the present disclosure, the similarity index may also be the correlation coefficient of the candidate transverse section image and the transverse section template image, namely:

$$E = \frac{\sum_{I_L, I_R \in \Omega} I_L I_R}{\sqrt{\sum_{I_L \in \Omega} I_L^2} \sqrt{\sum_{I_R \in \Omega} I_R^2}}, \quad (5)$$

Wherein E is the similarity index, $\Omega$ is the image space of the candidate transverse section image, $I_L$ is the data value of the point of the candidate transverse section image, $I_R$ is the data value of the point of the transverse section template image corresponding to the point of the candidate transverse section image.

The definition of the similarity index includes but not limited to aforementioned two methods, and it may also use other similar definition, for example, the Euclidean Distance between the candidate transverse section image and the transverse section template image, Cosine Similarity between the candidate transverse section image and the transverse section template image, etc. The present disclosure is not limited to the specific calculation manner of how to define the similarity index, and the similarity index can be used in each embodiment of the present disclosure as long as it is based on measuring the similarity between the candidate transverse section image and the transverse section template image.

In addition, in aforementioned step S23, the calculation of the similarity index between the candidate transverse section image and the transverse section template image can be specifically realized based on similarity judgment among the images. There will be different types of similarity index calculation manner for different methods of judging similarity between the images.

For example, in one embodiment of the present disclosure, the similarity among the images can be calculated based on characteristic expression extracted according to images, specifically including the following steps:

Firstly, extracting image characteristic from the transverse section template image to form a first characteristic quantity;

After that, extracting an image characteristic from each candidate transverse section image of the candidate transverse section image set as a second characteristic quantity respectively to form a set of second characteristic quantities. The method for extracting the second characteristic quantity can be identical to the method for extracting the first characteristic quantity, namely the method for extracting image characteristic from the transverse section template image can be identical to the method for extracting an image characteristic from each candidate transverse section image.

Finally, calculating a likelihood between each second characteristic quantity of the set of second characteristic quantities and the first characteristic quantity respectively to form the set of similarity indexes.

In one or more embodiments, measuring the similarity index between the candidate transverse section image and the transverse section template image by utilizing the likelihood between the first characteristic quantity and the second characteristic quantity.

In the embodiment, the manifestation of the first characteristic quantity and the second characteristic quantity can be different based on different image characteristic extracting algorithm. The first characteristic quantity and the second characteristic quantity represent the image characteristic expression obtained after training or analysis aiming at a target by utilizing image characteristic extracting algorithm.

For example, in one embodiment, based on a template match method, extracting image gray scale characteristic of the transverse section template image, or extracting image gray scale characteristic from the transverse section template image been processed with arithmetic processing such as convolution by utilizing one or more characteristic extracting operator, or combination of image gray scale characteristic of the former two, to be the first characteristic quantity; extracting image gray scale characteristic of each candidate transverse section image, or extracting the image characteristic from the candidate transverse section image set been processed with arithmetic processing such as convolution by utilizing one or more characteristic extracting operators, or combination of image gray scale characteristic of the former two, to be the second characteristic quantity respectively to form a set of second characteristic quantities to calculate the likelihood between the first characteristic quantity and the second characteristic quantity to characterize the similarity index among images.

The image obtained after convolution based on characteristic extracting operator and image data (such as the transverse section template image or the candidate transverse section image set), the image been processed with convolution contains the extracted section characteristic region. For example, the size of a template image is M*N, namely, spreading it to be a column vector sized M*N, which is the gray scale characteristic of the template image. Some templates (assuming there are n templates) also can be adopted for convolution of the image to obtain n convolution images sized M*N, and spread these images to column vectors sized M*N and add it to the gray scale characteristic to form (n+1)*M*N column vectors as the image gray scale characteristic of such template images. Then, a transverse section template image can be spread to form a column vector, to obtain a column vector sized M*N of gray scale characteristic of a transverse section template image as the first characteristic quantity; also, by utilizing the characteristic extracting operator to perform arithmetic processing such as convolution to the transverse section template image, and adding image gray scale characteristic for characteristic extracting to obtain the image gray scale characteristic of the transverse section template image, namely, the spread (n+1)*M*N dimensional column vectors after convolution of the transverse section template image as the first characteristic quantity, the former may base on a standard transverse section image, and the latter may base on a plurality of standard transverse section images collected at the same anatomical position of a plurality of sample bodies.

In one or more embodiments of the present disclosure, when performing convolution on the 3D volume data brought into the transverse section template image or the candidate transverse section image set by using characteristic extracting operator, convolutions can be respectively made on each image frame constructing 3D volume data by using 2D characteristic extracting operator respectively, after that, combining the image frame been processed with convolution to form 3D volume data after convolution processing; or 3D characteristic extracting operator may be directly designed, and directly using the 3D characteristic extracting operator to perform convolution with the 3D volume data. The specific steps for convolution calculation are well-known in the field, which will not be described in details herein.

In one or more embodiments of the present disclosure, characteristic extracting operator may be designed according to the image characteristic to be extracted. If adopting the following operator (included but not limited to), edge characteristic of the image may be extracted, and one or a plurality of the following characteristic extracting operators may be used:

$$\begin{bmatrix} -1 & 0 & 1 \\ -2 & 0 & 2 \\ -1 & 0 & 1 \end{bmatrix}. \tag{6}$$

$$\begin{bmatrix} -1 & \cdots & -1 \\ & 0 & \\ 2 & \cdots & 2 \\ & 0 & \\ -1 & \cdots & -1 \end{bmatrix}. \tag{7}$$

$$\begin{bmatrix} 1 & 2 & 1 \\ 0 & 0 & 0 \\ -1 & -2 & -1 \end{bmatrix}. \tag{8}$$

In one or more embodiments of the present disclosure, characteristic extracting operators obtained through deforming the aforementioned characteristic extracting operator by transposition (matrix transposition) and/or rotation, or combination thereof may be used, other suitable characteristic extracting operator may also be used, such as Roberts operator, Laplace Gaussian operator and its deformation, etc.

In one or more embodiments of the present disclosure, similarly, 3D characteristic extracting operator may be directly designed, which will not be described in details herein.

In one or more embodiments of the present disclosure, the size of the characteristic extracting operator (2D or 3D) can be set according to need.

When extracting the first characteristic quantity based on one embodiment described above, such as the column vector sized M*N or (n+1)*M*N, further based on the same or similar characteristic extracting method, extracting the corresponding second characteristic quantity of each candidate transverse section image of the candidate transverse section image set, each second characteristic quantity may also be expressed with column vector sized M*N or (n+1)*M*N, and obtaining a set of second characteristic quantities based on the same characteristic extracting method analyzing the candidate transverse section image set. Based on the first characteristic quantity and the second characteristic quantity, analyzes and calculates a similarity index between each candidate transverse section image of the candidate transverse section image set and the template image to obtain a set of similarity indexes. The corresponding second characteristic quantity of each candidate transverse section image of the candidate transverse section image set all need likelihood calculation with the first characteristic quantity obtained above, by utilizing the calculation of the likelihood between the first characteristic quantity and the second characteristic quantity to measure the similarity index between each candidate transverse section image and the template image. For example, in one embodiment of the present disclosure, define the likelihood between the second characteristic quantity and the first characteristic quantity as the absolute value of the difference between the second characteristic quantity and the first characteristic quantity. If the first characteristic quantity and the second characteristic quantity are expressed by the N dimensional column vectors (≥1), then during specific calculation, the equation (9) as described below can be adopted, and the likelihood E between the second characteristic quantity and the first characteristic quantity represents the sum of the absolute value of element value difference at each corresponding position of the second characteristic quantity and the first characteristic quantity $$E=\Sigma |I_{Li}-I_{Ri}|, I_{Li} \in I_L, I_{Ri} \in I_R \quad \text{Equation (9)}$$

Wherein $I_L$ represents the second characteristic quantity, $I_{Li}$ represents the element value at the i position of the second characteristic quantity, $I_R$ represents the first characteristic quantity, $I_{Ri}$ represents the element value at the i position of the first characteristic quantity. It can be observed from the definition that the smaller of the E value obtained by calculating according to the equation (9), it means the second characteristic quantity is more similar to the first characteristic quantity, that is, the candidate transverse section image is more similar to the template image.

Furthermore, in another embodiment of the present disclosure, utilizing the correlation coefficient between the second characteristic quantity and the first characteristic quantity to define the likelihood E between the second characteristic quantity and the first characteristic quantity, which may be shown as the following equation (10), $$E = \frac{\sum I_L I_R}{\sqrt{\sum I_L^2} \sqrt{\sum I_R^2}} \quad \text{Equation (10)}$$

Wherein, $I_L$ represents the second characteristic quantity, $I_R$ represents the first characteristic quantity. If the E value is more close to 1, it means the second characteristic quantity is more similar to the first characteristic quantity, that is, the candidate transverse section image is more similar to the template image.

Besides the above several definition methods for the likelihood, the aforementioned calculation method of similarity index may be also included, such as, methods including the Euclidean Distance and Cosine Similarity index between second characteristic quantity and first characteristic quantity, all of which may achieve similar effect. The disclosure is not limited to how to define the specific calculation method for the likelihood, and the likelihood can all be applied in each embodiment of the disclosure as long as it is constructed based on the first characteristic quantity and the second characteristic quantity.

For another example, in another embodiment of the present disclosure, extracting image gray scale, or projection characteristic such as transformation of the gray scale in the spatial domain based on linear projection characteristic extracting method or nonlinear projection characteristic extracting method, to express the first characteristic quantity and the second characteristic quantity. Characteristic extracting methods obtained based on principal component analysis and Fisher linear distinguish analysis are collectively called linear projection analysis, and nonlinear projection characteristic extracting method may include: kernel principal component analysis (KPCA). Furthermore, when calculating a similarity index between each candidate transverse section image and the transverse section template image in step S23, based on projection characteristic extracting method to extract the projection characteristic of the image gray scale respectively from transverse section template images to form the first characteristic quantity, and extract the projection characteristic of the image gray scale from each candidate transverse section image to form the second characteristic quantity. For example, in one embodiment of the present disclosure, based on principal component analysis (PCA), by finding projection characteristic that can mostly represent the initial data under the minimum mean square sense to be the extracted image gray scale characteristic for analyzing the similarity among the images, that is to say, extracting the projection characteristic based on principal component analysis. Take the extraction of projection characteristic from the transverse section template image as an example, the detailed specifications of projection characteristic extracting procedures may be shown as follows.

Firstly, extracting N standard transverse sections collected at the same anatomical position of N sample bodies among aforementioned transverse section template images as N training samples to construct training sample database, of which N is greater than or equal to 1.

After that, expressing each training sample of the training sample database by matrix after it is being spread out, and calculating the covariance matrix of the first matrix obtained after each training sample of the training sample database subtracts the average sample. For example, suppose there are N training samples of the training sample database, the image resolution of each training sample is W×H, and spreading each image to be a M dimensional length vector, M=W×H, then the image of the training database may be expressed as a M×N matrix, marked as $[I_1, \ldots, I_N]_{M \times N}$, of which, $I_i$ is the training sample vector, m is the average value of the training sample, namely, the average sample. The training sample of the training sample database subtracts the average sample to get a new training sample L with average value of 0, namely, the first matrix, as shown in equation (11):

$$L=[I_1-m, \ldots, I_N-m] \quad \text{Equation (11)}$$

Then the covariance matrix C of the first matrix may be expressed as the following equation (12):

$$C = \sum_{i=1}^{N} (I_i - m)(I_i - m)^T = LL^T \quad \text{Equation (12)}$$

Wherein $L^T$ is the transposition of the first matrix L.

Secondly, calculating the characteristic value of covariance matrix C and orthogonalized characteristic vector E (for example, basis of PCA), after that, taking the product of transposition matrix of characteristic vector E and the first matrix as the projected result (refer to the following equation (13) for details) of each training sample on the average sample, and taking the projected result as the first characteristic quantity. All need is to keep the maximum n characteristic values and its corresponding characteristic vector, and then find out the projected result F (namely characteristic or principal component of each training sample) of each training sample on the average sample, which maybe:

$$F_i = E^T(I_i - m) \quad \text{Equation (13)}$$

Wherein $E^T$ is the transposition of characteristic vector E, Fi is the first characteristic quantity of li, and the projection decreases the M*1 dimensional sample to n*1, thus eliminating the correlation between the high dimensional data, and the n*1 dimensional data may represent the initial data the mostly under least mean square sense, which can be regarded as the first characteristic quantity to represent the gray scale statistical characteristic extracted from the images. The above characteristic extracting is realized just based on a projection characteristic extracting method PCA, similarly, different characteristic vector E may be obtained by adopting different projection characteristic extracting methods, and the first characteristic quantity can be obtained by utilizing aforementioned equation (13), and the projection characteristic extracting method mentioned herein can also be LLP (Locality Preserving Projections), ICA (independent component analysis), or KPCA (Kernel PCA), etc.

Characteristic vector E, average sample m, and the first characteristic quantity are obtained through the characteristic extracting method of aforementioned a plurality of template images based on the equation (11) and (13), similarly, spreading each candidate transverse section image of the candidate transverse section image set to be a M dimensional vector $I_{test}$ based on the same characteristic extracting method as mentioned above, and projecting it on the characteristic vector E, namely, the equation (13) is deformed to be the form of the following equation (14).

$$F_j = E^T(I_{test} - m) \quad \text{Equation (14)}$$

Wherein, $F_j$ represents the corresponding characteristic of a M dimensional vector $I_{test}$ spread by each candidate transverse section image, also referred as second characteristic quantity, j represents the corresponding serial number of each candidate transverse section image of aforementioned candidate transverse section image set. Then, calculating the likelihood between the first characteristic quantity and the second characteristic quantity to obtain a set of similarity indexes, please refer to the likelihood calculation method of the first characteristic quantity and the second characteristic quantity in previous text for details, which will not be described herein again.

Based on aforementioned embodiments, no matter it is based on the template match method or projection characteristic extracting method, in another embodiment of the present disclosure, the steps for extracting image characteristic from transverse section template image include: extracting image gray scale characteristic from the standard transverse section image of the transverse section template image to form the first characteristic quantity. In addition, extracting the image gray scale characteristic from each candidate transverse section image by utilizing the same method for extracting the image gray scale characteristic from aforementioned standard transverse section image, to form aforementioned a set of second characteristic quantity.

Similarly, the corresponding image characteristic may be also extracted by combining the standard transverse section image of the transverse section template image with the non-standard transverse section image, which may be used for calculating the similarity index between each candidate transverse section image and the transverse section template image. Details are as follows.

In another embodiment of the present disclosure, automatically screening the section images having high similarity to the template image based on image classification model (such as image classifier or neural network model), please refer to the following steps for details:

Firstly, constructing image classification model, and utilizing the transverse section template image to train the image classification model to obtain trained image classification model. The transverse section template image may include: at least a standard transverse section image collected from at least a sample body which is related to the anatomical position and at least a non-standard transverse section image collected from at least a sample body which is related to the anatomical position. The image classification model refers to the model that can automatically classify and tag the input images to obtain classification tag, such as image classifier or neural network model.

After that, inputting each candidate transverse section image of the candidate transverse section image set to the trained image classification model respectively to obtain the corresponding classification tag of each candidate transverse section image and form a set of classification tags as the set of similarity indexes.

In one embodiment, measure the similarity among the images by utilizing the classification tags obtained by image classification model, to calculate the similarity index between the candidate transverse section image and the transverse section template image. The trained image classification model includes known parameter configuration, which can be used for automatic classification of the input images. Use a trained characteristic extracting model to automatically recognize whether each candidate transverse section image of the candidate transverse section image set is similar to the standard transverse section image to obtain a corresponding classification tag, and such classification tag is used for characterizing whether the input candidate transverse section image is similar to the standard transverse section image.

For example, take the neural network model constructed based on image classification method as an example to explain an implementation in details.

Firstly, a plurality of standard transverse section images (hereinafter referred to the positive sample, and assuming the number of the positive sample is N1) and non-standard transverse section images (hereinafter referred to the negative sample, and assuming the number of the negative sample is N1) collected based on a plurality of sample bodies constructs N samples and simultaneously are given corresponding classification tags. For example, N samples N=N1+N2, in order to express more easily, N samples is represented by $x_j$, the classification tag of the sample is represented by $t_j$, $t_j=1$ means the sample is a negative sample, and $t_j=0$ means the sample is a positive sample.

After that, inputting the N samples and its corresponding classification tags into the neural network model to minimize the error between output classification tags obtained according to the neural network model and the actual tags (namely the input classification tags), to obtain the trained neural network model, at this time the neural network model has already been configured with relevant parameter value.

Figure 9:
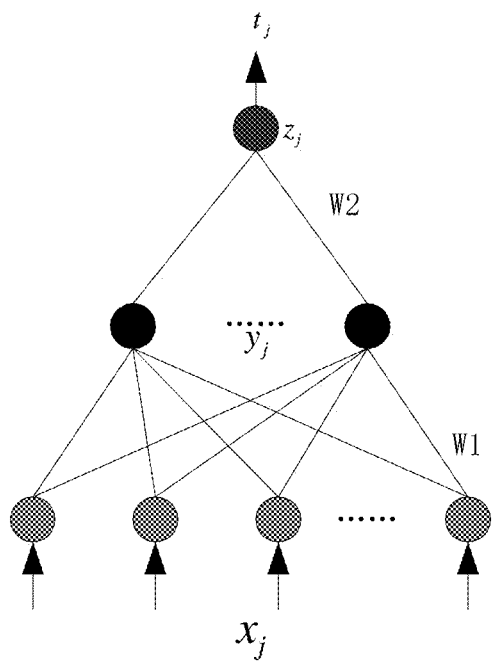
FIG. 9 is a schematic diagram of a neural network.

FIG. 9 is a schematic diagram of the neural network, take a three-layer network as an example, input the sample $x_j$, and after network mapping $y_j=f(W_1 x_j)$, $z_j=f(W_2 y_j)$, obtain an output value $z_j$ to represent the classification tag, of which, framing the neural network model by constructing a function model $f(x)$, and the function model $f(x)$ may be set according to needs, such as adopting a sigmoid function, as shown in following equation (15).

$$f(x) = \frac{1}{1+e^{-x}} \quad \text{Equation (15)}$$

The definition of the minimized neural network output error is shown in following equation (16):

$$\min \sum_{j=1}^{N} |t_j - z_j| \quad \text{Equation (16)}$$

Solving the equation (16) to minimize $$\min \sum_{j=1}^{N} |t_j - z_j|,$$

which may obtain weight W1 and weight W2 of the neural network model, that is, the relevant parameters of the neural network model, which include weight W1 of neural network model and weight W2 of classification tag function. The solving method of above equation (16) may adopt gradient descent method.

Another method may also be adopted, that is, the method for calculating the above weight W1 and W2 of neural network model is randomization method, as shown below.

Firstly, setting weight W1 of neural network model $y=f(W_1x)$ to be a random matrix, that is the value of W1 is generated randomly.

After that, utilizing the above N samples $x=[x_1, x_2, \ldots x_N]$ and inputting them into neural network model $y=f(W_1x)$ to calculate $y_i$, $y_i \in [y_1, y_2, \ldots y_N]$;

Secondly, calculating the weight W2 according to the classification tag function represented by equation $t=f(W_2y)$; of which, $y=[y_1, y_2, \ldots y_N]$, $t=[t_1, t_2, \ldots t_N]$ represent classification tag of samples.

After randomly generating the weight W1 according to the above method, weight W2 only needs to be obtained by solving equation, and does not need to iterate, thus the calculation is quick.

After respectively inputting the each candidate transverse section image of the candidate transverse section image set into the trained neural network model (namely a neural network model with known weight W1 and weight W2), outputting the corresponding classification tag, and regarding the output classification tag result as the calculated similarity index between the candidate transverse section image and the template image, or defining the similarity index according to the output result of classification tag. It may obtain a set of similarity indexes for each of all the candidate transverse section images correspondingly. For example, when inputting a candidate transverse section image into the trained neural network model, the output classification tag z=1, which means that the candidate transverse section image is judged to be a negative sample, and its similarity index may be defined as 0; otherwise, the output classification tag z=0, it represents that the candidate transverse section image is judged to be a positive sample, and its similarity index may be defined as 1. It should be noted that the network layer and number of intermediate nodes are adjustable parameters if neural network method is adopted.

Similarly, image classifiers such as SVM image classifier or its deformation can also be trained base on the similar method of above neural network model by utilizing a plurality of standard transverse section images and non-standard transverse section images. Classify and tag the candidate transverse section image of the candidate transverse section image set base on the trained SVM image classifier, to measure the similarity between the candidate transverse section image and template image. Certainly, it may also use the image characteristic of the standard transverse section images obtained at different anatomical positions to restrain the above SVM image classifier, the neural network model or deformation thereof, thus to form an improved image classification model, which can still be regarded as the image classification model constructed above, and applied in one or more embodiments of the present disclosure.

In embodiments of the present disclosure, in step S24, calculating the similarity index for each of all the candidate transverse section images to form a set of similarity indexes. Then, select the similarity index which satisfies the image characteristic condition from the set of similarity indexes. In one or more embodiments of the present disclosure, the candidate transverse section image corresponding to the similarity index which satisfies the image characteristic is regarded as the transverse section to be detected. Here, the 'image characteristic conditions' can be the conditions that represent the similarity between the candidate transverse section image and the template image is most optimal. The image characteristic varies according to different calculation methods of similarity index. For example, for the above similarity index calculated according to equation (4) and (9), it can be seen that the smaller the E value (namely the similarity index) is, the more similar is the image pixels of the candidate transverse section image and image pixels of the template image, namely the similarity is better, thus, at this moment, the image characteristic conditions can be 'minimum similarity index'.

Whereas for the foregoing similarity index calculated according to equation (5) and (10), the bigger (as for equation (5), that is the E value is closer to 1) the E value (namely similarity index), the higher similarity between image pixels of the candidate transverse section image and image pixels of the template image, namely the similarity is better, thus, at this moment, the image characteristic conditions can be 'maximum similarity index' or 'similarity index is the closest to 1'.

When calculating the similarity index according to other methods, the image characteristic can also be defined similarly. For example, when the similarity index is the Euclidean Distance between the candidate transverse section image and the template image or the Euclidean Distance between the first characteristic quantity and the second characteristic quantity, image characteristic conditions can be 'minimum similarity index', namely, the smaller (that is, Euclidean Distance is smaller) the similarity index, then the higher similarity between the candidate transverse section image and the template image; when the similarity index is the Cosine Similarity between the candidate transverse section image and the template image or the Cosine Similarity between the first characteristic quantity and the second characteristic quantity, the image characteristic conditions can be 'maximum similarity index', namely, the bigger (that is, Cosine Similarity is bigger) the similarity index, then the higher similarity between the candidate transverse section image and the template image, etc.

For another example, based on image classification method to construct characteristic extracting models such as an image classifier (e.g. the SVM image classifier), or neural network model, then the classification tag output by utilizing the trained characteristic extracting model is regarded as the similarity index, if using '1' to represent being judged to be a positive sample, and '0' to represent being judged to be a negative sample, the image characteristic conditions can be 'the similarity index is 1', namely the similarity at this time is 1 (that is, judged to be a positive sample), if judged to be a positive sample, then the higher similarity between the candidate transverse section image and the standard transverse section image for correctly characterizing the target tissues. However, in actual implementation, sample images close to the actual optimal section (namely the section at the correct anatomical position) are usually judged to be the positive samples, therefore, when at least two candidate transverse section images are judged to be positive samples, the region with most concentrated judgment of positive sample can be selected and output as the transverse section to be detected, for example, calculating the average position of the candidate transverse section images that are judged to be positive samples, and selecting the corresponding transverse section outputs from the 3D volume data according to the average position as the transverse sections to be detected for displaying. Or also, according to all samples that are judged to be positive samples, adopting kmeans algorithm to calculate the center of all samples, and regarding the candidate transverse section image corresponding to the center as the transverse sections to be detected for displaying. Kmeans algorithm belongs to existing technology, which will not be described in details herein.

In other words, when the detected transverse section is non-unique according to the transverse section template image related to an identical anatomical position, namely, when the number of similarity indexes which satisfy the image characteristic condition selected from a set of similarity indexes is greater than 1, then choosing the above transverse section to be detected from the candidate transverse section images corresponding to the selected similarity indexes. For example, based on the position of the candidate transverse section image corresponding to the selected similarity index in 3D volume data or position at an arbitrary sagittal section and/or coronal section, calculating the average position, selecting the corresponding transverse section from the 3D volume data according to the average position to output as the transverse section to be detected for displaying. Or, bring the candidate transverse section image corresponding to the selected similarity index into a sample set, adopting kmeans algorithm to calculate the center of the sample set, and choosing the candidate transverse section image output corresponding to the center as the transverse section to be detected for displaying.

After the above step S20, a transverse section to be detected is obtained, however, according to the image characteristic extracted from the transverse section template image related to the same anatomical position, a candidate transverse section image with the above image characteristic may be selected from the candidate transverse section image set as a transverse section to be detected. In order to utilize the present disclosure to simultaneously and automatically detect a plurality of transverse sections to be detected, when making use of the image characteristic extracted from the transverse section template image related to at least an anatomical position of the head of the target body, to choose the candidate transverse section images with the corresponding image characteristic from the candidate transverse section image set as a plurality of transverse sections to be detected, and execute the step S22 repeatedly based on the transverse section template images related to different anatomical positions. As for candidate transverse section image set, it may adopt the candidate transverse section image set obtained based on one-time implementation of the step S21, or every time executing the step S22, re-executing the step S21 to obtain a candidate transverse section image set. For example, when automatically detecting and displaying a cerebellum section, it may first obtain a candidate transverse section image set based on the step S21, then obtain the cerebellum section for displaying by executing the step S22 based on the cerebellum section template image, and when simultaneously displaying the lateral ventricle section, it may first base on the candidate transverse section image obtained before, then obtain the lateral ventricle section for displaying by executing the step S22 based on the lateral ventricle section template image.

Taking the following ultrasonic image of a fetal brain as an example to introduce the automatic detection method related to median sagittal section image in details.

Figure 10:
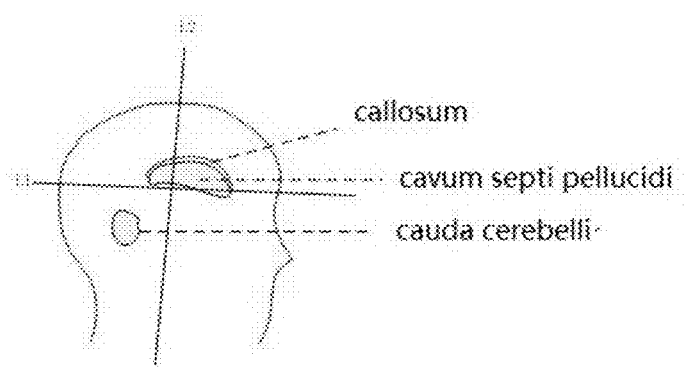
FIG. 10 is a schematic diagram of the median sagittal section image of a fetal brain.
Figure 11:
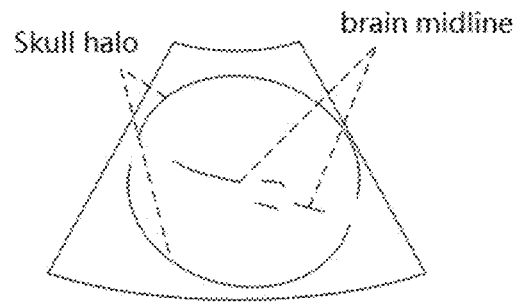
FIG. 11 is a schematic diagram of the section L1 shown in FIG. 10.
Figure 12:
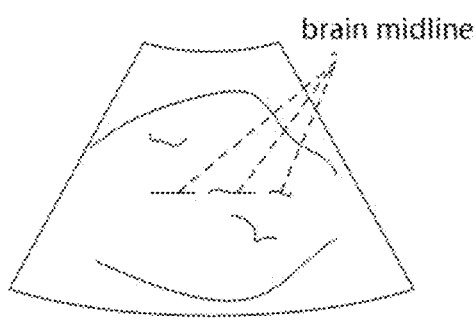
FIG. 12 is a schematic diagram of the section L2 shown in FIG. 10.

FIG. 10 and FIG. 12 respectively and schematically display the schematic diagram of a section L1 and a section L2 both perpendicular to the median sagittal section image of a fetal brain.

The median sagittal section image has some special characteristic in 3D images of a fetal brain, for example, among all the sections in 3D images of a fetal brain, the median sagittal section image overall has much bigger gray scale value than the peripheral region, in other words, in 3D images of a fetal brain, the median sagittal section image appear as a section of which the gray scale value is obviously bigger than the gray scale value of the region around it, or, the median sagittal section image is much brighter than the peripheral region in 3D images of a 3D fetal brain; or, in a fetal brain, the structures of two sides of the median sagittal section are approximately symmetrical, thus, in 3D images of a fetal brain, the image data of two sides of the median sagittal section image shows approximate symmetry; or, in a fetal brain, the median sagittal section is in the middle position of the brain, and in 3D images of a fetal brain, other sections intersecting with the median sagittal section image contain information of intersection position of the other section with the median sagittal section image, and in images of the other section, the intersection line of such section with the median sagittal section image appears as a relative brighter line, that is a brain midline. Assemble of these brain midlines construct a median sagittal section image; etc. In some embodiments of the present disclosure, these characteristic of the median sagittal section image of a fetal brain is used for detecting or identifying the median sagittal section image from the 3D volume data of a fetal brain.

Thus, in some embodiments of the present disclosure, in step S11, according to the median sagittal section image characteristic (such as, image characteristic as mentioned above, e.g. the gray scale characteristic) of a fetal brain, detecting the median sagittal section image from the 3D volume data obtained in step S10.

In one or more embodiment of the present disclosure, the aforementioned 'detecting the median sagittal section image from the 3D volume data obtained in step S10 may refer to detecting from all 3D volume data of a fetal brain, or detecting from partial 3D volume data of a fetal brain, for example, it may detect in the region where the median sagittal section image is most likely to exist, and discard the region where the median sagittal section image is obviously unlikely to exist. For example, as the median sagittal section image of a fetal brain is a vertical section (namely a section at the direction from head to neck) located in the middle of a fetal brain, thus the median sagittal section image obviously cannot exist in some regions located at the boundaries of head, and such region can be excluded from the detection range.

In some embodiments of the present disclosure, various methods can be used to detect the median sagittal section according to the 3D volume data. For example, as mentioned before, in 3D volume data, the median sagittal section image shows the characteristic that the gray scale value thereof is bigger than that of the peripheral region. Therefore, in one embodiment of the present disclosure, detect the median sagittal section from the 3D volume data by utilizing such characteristic of the median sagittal section image.

Figure 13:
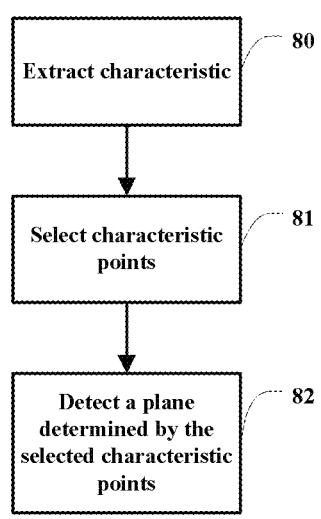
FIG. 13 is a schematic flow chart of a step of detecting the median sagittal section image according to one embodiment of the present disclosure.

In one embodiment of the present disclosure, a flowchart diagram of detecting the median sagittal section according to the 3D volume data is shown in FIG. 13.

In some embodiment of the present disclosure, in step 80, it may firstly extract from 3D volume data the sagittal section characteristic region satisfying the condition that the gray scale value within the plane is bigger than that of the two sides of the plane.

In other words, in one embodiment of the present disclosure, extract some characteristic regions from the 3D volume data, and in the method of embodiment of the present disclosure, these needed characteristic regions represent the plane regions satisfying the condition that the gray scale value within the plane is bigger than that of the two sides of the plane, and such extracted characteristic regions are the sagittal section characteristic regions needed. Thus, good detection effect of the median sagittal section image may be obtained by sufficiently utilizing the characteristic 'the median sagittal section image appears as a section of which gray scale value is obviously bigger than that of its peripheral region'.

In embodiments of the present disclosure, such sagittal section characteristic region may be extracted from 3D volume data by utilizing various suitable methods. For example, in one embodiment, it may use characteristic extracting operator to perform convolution with the 3D volume data to obtain images after convolution processing, which contains the extracted sagittal section characteristic region.

In embodiments of the present disclosure, when performing convolution on the 3D volume data by using the characteristic extracting operator, convolutions can be respectively made on each image frame constructing the 3D volume data by using 2D characteristic extracting operator respectively, after that, combining the image frames been processed with convolution to form the 3D volume data after convolution processing; or 3D characteristic extracting operator may be directly designed, and directly using the 3D characteristic extracting operator to perform convolution with the 3D volume data. The specific steps for convolution calculation are well-known in the field, thus will not be described in details herein.

In one or more embodiments of the present disclosure, the characteristic extracting operator may be designed according to the image characteristic to be extracted. For example, as mentioned in previous embodiment, it needs to extract the sagittal section characteristic region that the gray scale value within the region is bigger than that of the two sides of the region. Thus, one or a plurality of the following characteristic extracting operators may be used:

$$\begin{bmatrix} -1 & -1 & -1 \\ 2 & 2 & 2 \\ -1 & -1 & -1 \end{bmatrix}; \quad (16)$$

$$\begin{bmatrix} -1 & \ldots & -1 \\ & 0 & \\ 2 & \ldots & 2 \\ & 0 & \\ -1 & \ldots & -1 \end{bmatrix}; \quad (17)$$

$$\begin{bmatrix} -1 \\ 0 \\ \ldots \\ 0 \\ 2 \\ 0 \\ \ldots \\ 0 \\ -1 \end{bmatrix}; \quad (18)$$

$$\begin{bmatrix} 1 & 2 & 1 \\ 0 & 0 & 0 \\ -1 & -2 & -1 \end{bmatrix}; \quad (19)$$

$$\begin{bmatrix} -1 & -2 & -1 \\ 0 & 0 & 0 \\ 1 & 2 & 1 \end{bmatrix}. \quad (20)$$

In embodiments of the present disclosure, the characteristic extracting operators obtained through deforming the aforementioned characteristic extracting operator by transposition (matrix transposition) and/or rotation, or combination thereof may be used, and please see relevant specifications related to the characteristic extracting operator in previous text.

After extracting the sagittal section characteristic region in step 80, select the characteristic point from the extracted sagittal section characteristic regions whose value satisfies specific conditions in step 81, for example, select at least three characteristic points. Record the characteristic point parameters of the selected characteristic points and these characteristic point parameters can be used in subsequent steps.

In embodiments of the present disclosure, the characteristic point parameter herein may include the coordinates and/or value (such as, gray scale value or the result value after convolution, etc) of the characteristic point.

In embodiment of the present disclosure, the foregoing specific condition may be determined by the nature of characteristic extracting operator. For example, if adopting the foregoing characteristic extracting operators (16)~(20), the foregoing specific condition may be set as the point that the value is bigger than a threshold value among the convolution results, such threshold value may be empirical parameter, and may be determined according to actual needs.

In addition, in embodiment of the present disclosure, in order to reduce the pressure for subsequent plane detection steps (will be described in details hereinafter), and reduce the influence of noise, it may remove some obvious points unlikely to be within the head according to certain prior knowledge. For example, the head is usually located in the middle of the 3D volume data. Therefore, it may only select the center of the 3D volume data as center of a sphere, and points within a ball or spheroid with a radius of some threshold value as characteristic points. The threshold value herein may be determined according to experience or actual situation.

After selecting the characteristic points in step 81, these selected characteristic points can usually determine a plane, in some embodiments of the present disclosure, it is considered that this is the plane where the median sagittal section image is located, and in 3D volume data, the section coincided with such plane is the median sagittal section image of a fetal brain. Therefore, in embodiments of the present disclosure, in step 82, detecting the plane determined by these selected characteristic points is to determine the plane where the median sagittal section image of a fetal brain is located.

Determining a plane according to a plurality of characteristic points may be realized by using various methods, such as weighting Hough transformation, radon Hough transformation, least square estimation method, Radon transformation, etc.

For example, in one embodiment, it may use weighting Hough transformation to detect the planes determined by these selected characteristic points, which will be described in details hereinafter.

In a 3D space, plane equation may be represented by general expressions aX+bY+cZ+d=0 or Z=aX+bY+c or Y=aX+bZ+c, wherein, a, b, c, and d are the plane parameters for determining a plane.

In the 3D space, plane equation may also be represented by the following plane standard expression:

$$\rho = \cos\theta \cos\varphi X + \sin\theta \cos\varphi Y + \sin\varphi Z \quad (21).$$

Figure 14:
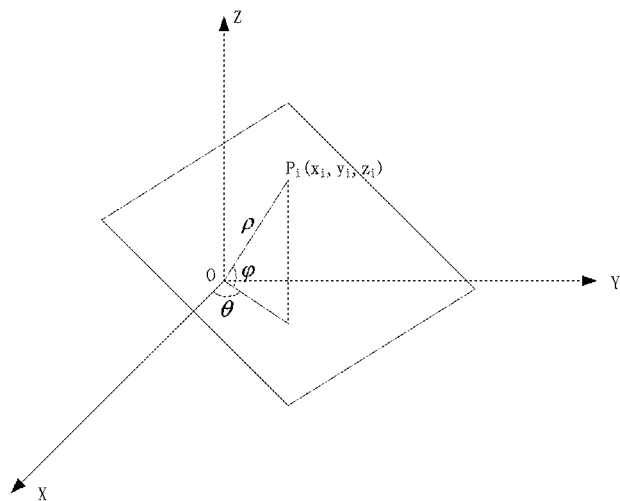
FIG. 14 is a schematic diagram of planes in the 3D space and plane parameters.

Wherein, equation (21), $\theta, \varphi, \rho$ are plane parameters, and their meanings can be as shown in FIG. 14, and a set of parameters $\theta, \varphi, \rho$ can determine a plane. The plane parameters $\theta, \varphi, \rho$ in equation (21) have their own value ranges, and the value ranges are related to the setting mode of the 3D Cartesian coordinates system. For example, as for 3D volume data, if the origin position of 3D Cartesian coordinates system is different, then the value range of the corresponding plane parameter is also different.

For example, in embodiment as shown in FIG. 14, the value range of parameter $\rho$ may be expressed as follows:

$$0 \le \rho \le \sqrt{(W-1)^2 + (H-1)^2 + (F-1)^2} \quad (22).$$

W, H, F represent the size of the 3D volume data, wherein, F is the quantity of image frame of the 3D volume data, W is the width of the image frame, and H is the height of the image frame.

It is easy to understand that when setting the 3D Cartesian coordinates system by other methods, the value ranges of plane parameters $\theta, \varphi, \rho$ will be accordingly be other values.

In 3D space corresponding to the 3D volume data, passing through a point, there will be countless planes, namely corresponding to countless $\theta, \varphi, \rho$, thus creating a new parameter space, which is called $\theta-\varphi-\rho$ space herein, also is the Hough space, the idea of Hough transformation is to project each point of original 3D space corresponding to the 3D volume data onto Hough space, and through detecting the peak value of Hough space, the peak value thereof corresponds to the plane of the original 3D space corresponding to the 3D volume data.

Figure 15:
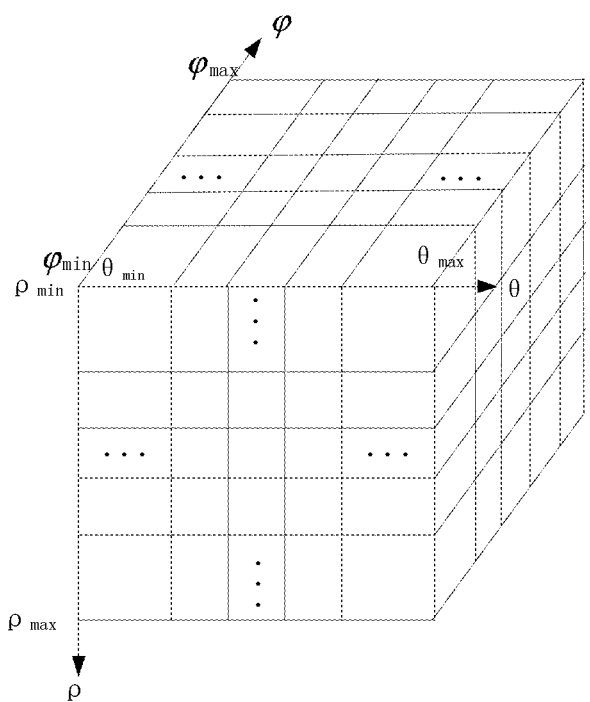
FIG. 15 is a schematic diagram of a 3D Hough matrix according to one embodiment of the present disclosure.

In one embodiment of the present disclosure, $\theta, \varphi, \rho$ are continuous parameters, therefore it may sample the $\theta, \varphi, \rho$, and subdivide the $\theta-\varphi-\rho$ into different units (as shown in FIG. 15). Thus, steps for weighting Hough transformation are as follows:

S111: calculating value range of the parameter and step-length of sampling. The value range of parameter $\rho$ can be expressed as equation 21, the maximum value range of $\theta, \varphi$ may be determined by referring to FIG. 14, for example, $0° \le \theta < 360°$, $-90° \le \varphi \le 90°$.

In some embodiments of the present disclosure, it may also narrow down the value range according to some prior knowledge.

Setting the ultimate value range to be $\theta_{min} \le \theta \le \theta_{max}$, $\varphi_{min} \le \varphi \le \varphi_{max}$, $\rho_{min} \le \rho \le \rho_{max}$, and sampling step-length $\theta_{step}$, $\varphi_{step}, \rho_{step}$ may be determined according to actual needs of detection precision, for example, in one embodiment, $\theta_{step}=1, \varphi_{step}=1, \rho_{step}=2$. Certainly, other suitable values also may be given.

S112: generate the Hough matrix and have it initialized. Generate Hough matrix and have it initialized to be 0, the size of a 3D Hough matrix may be:

$$\frac{(\theta_{max}-\theta_{min})}{\theta_{step}} \times \frac{(\varphi_{max}-\varphi_{min})}{\varphi_{step}} \times \frac{(\rho_{max}-\rho_{min})}{\rho_{step}}. \quad (23)$$

In one embodiment of the present disclosure, it may also adopt three 1D (one dimension) Hough matrixes herein, and their sizes may respectively be expressed as $$\frac{(\theta_{max}-\theta_{min})}{\theta_{step}}, \frac{(\varphi_{max}-\varphi_{min})}{\varphi_{step}}, \frac{(\rho_{max}-\rho_{min})}{\rho_{step}}.$$

S113: parameter voting. Calculating the corresponding $\rho_l$ s for each selected characteristic point, and each $\theta_j$ and $\varphi_k$ within foregoing parameter value range:

$$\rho_l = \cos\theta_j \cos\varphi_k X_i + \sin\theta_j \cos\varphi_k Y_i + \sin\varphi_k Z_i \quad (24)$$

Wherein (Xi, Yi, Zi) is the coordinate of the i characteristic point Pi.

And update the Hough matrix to be:

$$H(\theta_j, \varphi_k, \rho_l) = H(\theta_j, \varphi_k, \rho_l) + Vi \quad (25),$$

Wherein, Vi is the value (such as, gray scale value or the result value after convolution, etc.) of the ith characteristic point Pi.

S114: peak value detection of the Hough matrix. Calculating $\theta, \varphi, \rho$ corresponding to maximum value of the Hough matrix H. Suppose the positions of maximum value in the Hough matrix H to be $\theta_j, \varphi_k, \rho_l$, then a plane detection result is:

$$\theta = \theta_j \theta_{step} + \theta_{min}$$

$$\varphi = \varphi_k \varphi_{step} + \varphi_{min}$$

$$\rho = \rho_l \rho_{step} + \rho_{min} \quad (26).$$

Here, as for the foregoing embodiments adopting three 1D Hough matrixes, it shall respectively calculate each $\theta, \varphi, \rho$ corresponding to the maximum value in Hough matrix.

In the embodiment, weighting Hough transformation considers that the contribution value of each characteristic point Pi of selected characteristic points to the plane detection is different, and the bigger its corresponding value Vi is, the greater the corresponding contribution of it in Hough matrix will be.

In embodiment of the present disclosure, the contribution difference of each characteristic point may not be considered, that is setting the value Vi of each characteristic point to be 1 in previous method. Now, it may still detect a plane determined by these characteristic points. Actually, the previous weighting Hough transformation now is degenerated into a traditional Hough transformation algorithm.

In embodiment of the present disclosure, it may use other plane detection methods. For example, in one embodiment, radon Hough transformation may be used to detect a plane determined by selected characteristic points. Specific steps of radon Hough transformation are as follows:

S121: calculating value range of the parameter and step-length of sampling. Calculating the value range of plane equation parameters $\theta,\varphi,\rho$ and step-length of sampling, and this step can be identical or similar to S111 in previous method.

S122: generate Hough matrix and have it initialized to be 0. Generate a 3D Hough matrix and have it initialized to be 0, and this step can be identical or similar to S112 in previous method.

S123: randomly select points. Randomly select three points from selected characteristic points.

S124: plane equation solving, calculate the plane parameter. Substitute the coordinates of the three points into plane equation to solve plane equation parameters $\theta,\varphi,\rho$, and plane equation parameter solving method is well-known by technician in the field, which will not be described in details herein.

S125: updating the Hough matrix. Add 1 to the solved $\theta,\varphi,\rho$ in the corresponding positions of Hough matrix.

S126: repeat step 123 to step 125 for N times. N is a preset parameter herein, which can be set according to actual needs. For example, in one embodiment, N can be 50000. Certainly, N may be other value herein.

S127: peak value detection of the Hough matrix. Calculating maximum position of value of Hough matrix, and its corresponding $\theta,\varphi,\rho$ are the plane detection result, which is detected plane.

In another embodiment of the present disclosure, steps of another method for detecting a plane determined by selected characteristic points (herein referred to as radon energy optimization) can be as follows:

S131: initializing optimum energy E_best=0

S132: randomly selecting points. Randomly select three points from the selected characteristic points.

S133: equation solving. Substitute the coordinates of the three points into plane equation to solve plane equation parameters $\theta,\varphi,\rho$.

S134: current energy E calculating. Calculates energy E whose plane distance is smaller than $\varepsilon$ solved in step S133 of the selected characteristic points.

The specific steps may be, for each characteristic point Pi of the selected characteristic points, calculating the distance from the point to the plane $(\theta,\varphi,\rho)$ solved in step S33, if the distance is smaller than $\varepsilon$, then accumulate the value Vi corresponding to the current characteristic point into energy E, namely E=E+Vi. $\varepsilon$ is a parameter, which can be set according to needs, for example, in one embodiment, it may set as $\varepsilon=5$, $\varepsilon$ may also be set as other values.

S135: energy updating. If current energy E>E_best, then modify E_best to E, and simultaneously update the current plane equation parameters into optimum plane equation parameters, otherwise jump to step 136.

S136: repeating step 132 to step 135 for N times, here N is the number of iterations, which can be set according to needs.

S137: outputting equation parameters. After finishing step S136, the plane equation parameters corresponding to the iteration with maximum energy are the detected plane equation parameters.

Thus, it detects a plane determined by selected characteristic points.

In the embodiment, in step 134, the value Vi of characteristic point may not be accumulated, but directly judge that if the distance from point Pi to the plane is smaller than $\varepsilon$, then E=E+1, that is to consider that the contribution of each characteristic point of selected characteristic points to the plane detection result is the same.

In the above embodiments, it adopts a expression method of the plane equation 21, and the plane detection is to calculate the coefficients $\theta,\varphi,\rho$ of the equation. But the expression form of the equation does not affect the implementation of algorithm described in the present disclosure, in fact, as for other forms of equation expression methods, such as aX+bY+cZ+d=0, or Z=aX+bY+c, or Y=aX+bZ+c, the above method is still applicable, and only may need simple modifications.

As mentioned before, and referring to FIG. 4, and FIG. 10 to FIG. 12, in the 3D image of a fetal brain, the median sagittal section image is a vertical section located in the midmost of a fetal head, other section intersecting with the median sagittal section image will contain information of intersection position of the section with the median sagittal section image, namely contains information of the intersection. In other section images, the intersection line of such section with the median sagittal section image shows a relative brighter line (as stated earlier, in 3D images or 3D data of a fetal brain, median sagittal section image shows a plane brighter than peripheral region), that is a brain midline, and the assemble of these brain midlines constructs a median sagittal section image. Thus, in some embodiments of the present disclosure, it may use such characteristic to detect median sagittal section image from 3D volume data.

Figure 16:
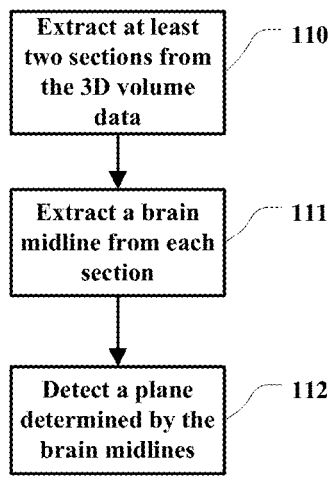
FIG. 16 is a schematic flow chart of a step of detecting the median sagittal section image according to another embodiment of the present disclosure.

For example, in one embodiment of the present disclosure, a flow diagram of detecting the median sagittal section according to 3D volume data is as shown in FIG. 16.

In the embodiment, in step 110, extract at least two sections from 3D volume data. There may be different methods for section extracting, for example, it may extract the planes parallel to section L1 in FIG. 10 and/or parallel to section L2 in FIG. 10; or extract any other sections, such as the sections forming certain angles with L2 and/or L1. The quantity/number for extracting the sections is not limited, at least two sections may be enough.

After extracting the sections, in step 111, extract the brain midline from each extracted section to obtain several straight lines representing the brain midlines.

Brain midline shows a straight line in a section, and its gray scale value is bigger than two sides, therefore, brain midline extraction can be realized by utilizing this characteristic.

In one embodiment of the present disclosure, as for every extracted section, extracting brain midline from it may include the following steps:

S40: extracting the brain midline characteristic region.

In this embodiment, it may first extract in the section the brain midline characteristic region conforming to foregoing brain midline characteristic, namely extract brain midline characteristic region satisfying that the gray scale value on the line is bigger than that of the two sides of the line. The extracting method for brain midline characteristic region may be similar to that for sagittal section characteristic region as mentioned before. For example, use the characteristic extracting operator to perform convolution to the section, and section after convolution includes the extracted brain midline characteristic region.

It should be understood that the 'line' and 'brain midline' referred herein should not be idealized to be explained as theoretical 'line', but actually region with certain width and/or thickness.

Here, characteristic extracting operator may be designed according to characteristic of the brain midline that needs to be extracted. In the embodiment, brain midline characteristic is similar to the foregoing median sagittal section characteristic, thus, it may use the operator similar to characteristic extracting operator in previous descriptions, for example, any operator similar to that of previous equation (16) to equation (20).

After extracting the brain midline characteristic region, select at least two characteristic points satisfying specific condition in brain midline characteristic region, and record the characteristic point parameters of such two characteristic points. Here, the characteristic point parameters may include coordinates and/or values (such as, gray scale value or value after convolution, etc) of the characteristic points or any other suitable parameters.

The specific condition mentioned herein may be determined according to the nature of adopted characteristic extracting operator. For example, if adopt the operator similar to the foregoing characteristic extracting operator (16)~(20), then the foregoing specific condition may be set as the point that the value is bigger than a threshold value among the convolution results, such threshold value may be empirical parameter, and may be determined according to actual needs.

S41: straight line detection.

These selected characteristic points usually determine a straight line. In embodiment of the present disclosure, it may detect the straight line determined by these selected characteristic points, and consider such straight line as the brain midline straight line in such section.

The methods such as weighting Hough transformation, radon Hough transformation, and radon energy optimization as mentioned in methods for determining a plane by detecting the selected characteristic points in 3D space in previous text can be used for detecting straight line in the step, may only need simple modifications in details.

For example, the standard equation for straight line is $\rho = \cos\theta X + \sin\theta Y$, with two parameters $\theta$, $\rho$ in total, a parameter $\varphi$ less compared with the plane equation. For example, when adopting weighing Hough transformation and radon Hough transformation, Hough matrix is two dimensional $\rho\_\theta$ matrix, in radon Hough transformation and radon energy optimization, only select two points randomly from the selected characteristic points for each iteration, a straight line can be calculated. The rest of the algorithm is basically the same with 3D plane detection method, which will not be described in details herein.

In addition, in embodiments of the present disclosure, it may use other methods to detect the selected characteristic point to determine a straight line, such as includes but not limited to Radon transformation, phase coded method, least square estimation, etc.

Based on the characteristic of the median sagittal section image in 3D images of a fetal brain, these extracted brain midline straight lines will determine a plane, which is the plane where the median sagittal section image is located.

Thus, after obtaining the brain midline straight lines of each extracted section in step 111, in step 112, detecting the plane determined by these brain midline straight lines to obtain the plane where the median sagittal section is located, that is the plane where the median sagittal section image of a fetal brain is located.

It may use many methods to detect the plane determined by these brain midline straight lines. For example, in one embodiment, it may select three points not collinear from the detected brain midline straight lines, substitute them into plane equation to calculate the parameters of plane equation; or execute the method several times, and at last make an average on the detection result as the ultimate detection result.

Another method may be selecting N points from the detected brain midline straight lines, and then fitting out the parameters the plane equation by least square estimation; or consider the extracted N points as input, and adopt methods mentioned by 3D plane detection such as Hough transformation, radon Hough transformation, radon energy optimization to detect the plane equation.

As mentioned above, and refers to FIG. 4, it can be seen that in the fetal brain, the structure of two sides of the median sagittal section are approximately symmetrical, therefore in the 3D image of the fetal brain, the image data of the two sides of the median sagittal section appear approximately symmetrical. Thus, in some embodiments of the present disclosure, it may use this characteristic of the median sagittal section image of the fetal brain to detect the median sagittal section in the 3D volume data. For example, it may select some candidate sections in the 3D volume data, after that, calculate the symmetry of the regions of two sides of the candidate section, the candidate section with the best symmetry of two sides can be regarded as the median sagittal section image needed.

Figure 17:
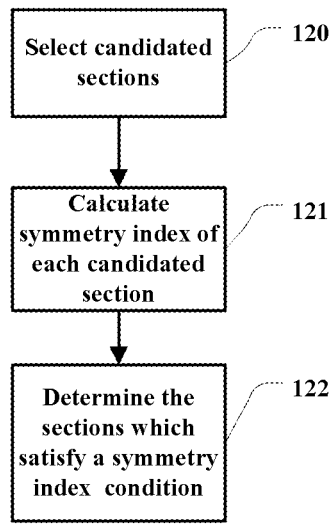
FIG. 17 is a schematic flow chart of a step of detecting the median sagittal section image according to still another embodiment of the present disclosure.

For example, in one embodiment of the present disclosure, schematic diagram of a flow chart of detecting the median sagittal section according to the 3D volume data may be shown in FIG. 17.

In step 120, it may select a plurality of candidate sections in the 3D volume data. The selection manner of the candidate sections may be determined according to different needs. For example, all the sections apart at certain intervals (or step-length) at one or a plurality of specific directions within certain range of the 3D volume data may be selected. The certain range can be the angle range relative to one or a plurality of lines and/or planes of the 3D volume data, and can also be the distance range relative to one or a plurality of points, lines and/or planes of the 3D volume data; the at one or a plurality of directions refer to the normal of the section in one or the plurality of directions; the intervals or step-length may be distance intervals or step-length, and also may be angle intervals or step-length.

In one embodiment of the present disclosure, all the sections apart at certain distance or step-length at one or a plurality of directions within all range of the 3D volume data can be selected; or, in other embodiment of the present disclosure, the candidate sections can be selected according to some prior knowledge, and candidate sections obviously do not containing the median sagittal section are discarded. For example, as the median sagittal section of fetus head is an vertical section located in middle position of the fetus head (that is, the section in the 3D volume data along the direction from the top of the fetus head to the neck of the fetus), therefore according to approximate direction of the fetus image in the 3D volume data, it may select the vertical sections approximately located in the middle position of the head as the candidate sections. In this disclosure, the sections in at least part of the 3D volume data along the direction that from the top of the fetus head to the neck of the fetus (that is, the sections parallel with the direction from the top of the fetus head to the neck of the fetus, or the sections whose normal is vertical to the direction that from the top of the fetus head to the neck of the fetus) are regarded as the vertical sections of the 3D volume data.

Therefore, a set of vertical sections may be selected from the 3D volume data as the set of candidate sections according to embodiments of the present disclosure. For example, selects a set of vertical sections approximately located in the middle position of the head (for example, all of the vertical sections apart at certain distance or step-length within a specific range in the middle position of the head) as the set of candidate sections.

Or, in the embodiments of the present disclosure, it may receive the user's input, and the user's input can indicate the possible scope where the median sagittal section image may be located, after that, it may select the sections in this scope which is indicated by the user as the candidate sections.

In the embodiments of the present disclosure, it may select all of the sections apart at certain step-length in the 3D volume data, that is, to perform traversing searching to all the sections within all range of the 3D volume data by certain step-length.

For example, in one embodiment, when using Equation (21) to represent the section equation, if the value ranges or scopes of the plane parameters $\theta, \varphi, \rho$ are designated and the values of the step-length $\theta_{step}, \varphi_{step}, \rho_{step}$ are designated, then the selection of the candidate sections is realized.

Similarly, when using the general expression $aX+bY+cZ+d=0$ or $Z=aX+bY+c$ or $Y=aX+bZ+c$ to represent the section equation, if scopes of the plane parameters a, b, c and d are designated, and step-length of each is designated, then the selection of the candidate sections is realized.

For example, when all of the sections apart at certain step-length in the 3D volume data are selected as the candidate sections, the value range of the parameter $\rho$ may be shown as equation (22), the maximum value range of $\theta, \varphi$, for example, may be $0° \leq \theta < 360°$ and $-90° \leq \varphi \leq 90°$ (refers to FIG. 14). It is easy to understand that, when the setting of the coordinates varies, value scopes of the parameters vary too.

The step-lengths $\theta_{step}, \varphi_{step}, \rho_{step}$ may be selected according to actual need of detection precision, and should not be limited by the present disclosure. For example, in one embodiment, it may be $\theta_{step}=1, \varphi_{step}=1, \rho_{step}=2$. It is easy to understand that, according to needed detection precision, the step-length also may be any other values.

After designating the candidate sections, in step 121, it may perform the traversing searching, by the selected step-length, to equations $\rho, \theta, \varphi$ of all the candidate sections within value scope of the plane parameter, and calculate the symmetry index of each candidate section.

The symmetry index is mainly used for measuring similarity of data of two sides of candidate section.

Therefore, for example, in one embodiment, for each candidate section, it may select at least a pair of first region and second region at different sides of the candidate section in the 3D volume data, and the first region and the second region are symmetrical about the candidate section, after that, it may use data of the first region and data of the second region to calculate the symmetry index of the candidate section.

Here the "data of the first region" refers to values the data points in the 3D volume data falling into the first region, similarly, the "data of the second region" refers to values the data points in the 3D volume data falling into the second region.

In one embodiments of the present disclosure, for each candidate section, it may select a plurality of pairs of first region and second region, calculate the symmetry index for each pair of first region and second region respectively, after that, according to a plurality of symmetry indexes corresponding to the plurality of pairs of first region and second region, obtain an ultimate symmetry index of the candidate section. For example, it may average the plurality of symmetry indexes to obtain a mean value as the symmetry index of the corresponding candidate section; or a weighted average of the plurality of symmetry indexes can be regarded as the corresponding symmetry index of the candidate section, wherein weighting coefficients may be determined according to position or other attribute of the selected pair of first region and second region, etc. In one embodiment of the present disclosure, the ultimate symmetry index of the candidate section may be a function of the symmetry indexes calculated respectively according to a plurality of pairs of first region and second region.

The symmetry index may be calculated according to multiple methods.

For example, in one embodiment, it may use a sum of absolute values of the difference of gray scales between corresponding points in the first region and second region as the symmetry index, which is:

$$E = \sum_{I_L, I_R \in \Omega} |I_L - I_R|, \tag{27}$$

Wherein, E is the symmetry index, $\Omega$ is the selected symmetrical first region and second region at two sides of the plane, $I_L$ is the data value of a point in the first region, $I_R$ is the data value of a point in the second region which is symmetrical with the point in the first region relative to the candidate section. Herein, the "corresponding points in the first region and second region" refers to points in the first region and second region which are symmetrical relative to the candidate section.

In one embodiment of the present disclosure, the symmetry index of the candidate section may be a correlation coefficient of the first region and second region, which is:

$$E = \frac{\sum_{I_L, I_R \in \Omega} I_L I_R}{\sqrt{\sum_{I_L \in \Omega} I_L^2} \sqrt{\sum_{I_R \in \Omega} I_R^2}}, \tag{28}$$

Wherein, E is the symmetry index, $\Omega$ is the selected symmetrical first region and second region at two sides of the plane, $I_L$ is the data value of a point in the first region, $I_R$ is the data value of a point in the second region which is symmetrical with the point in the first region relative to the candidate section.

The definition of the symmetry index includes but not limited to aforementioned two methods, and also may use other similar definitions, such as the Euclidean Distance of the first region and second region, and the Cosine Similarity Index of the first region and second region, etc.

For all of the candidate sections, a symmetry index of each candidate section is calculated to obtain a set of symmetry indexes. After that, select one or more characteristic symmetry indexes satisfy the characteristic condition from the set of symmetry indexes, in one or more embodiments of the present disclosure, the candidate section corresponding to the characteristic symmetry index can be regarded as a needed median sagittal section image of fetus head.

Herein, the "characteristic condition" may be a condition indicating the symmetry of a candidate section is optimum. The characteristic condition may vary according to different symmetry index calculating methods. For example, for the symmetry index calculated by using the equation (27), it can be seen that the smaller the value of E (that is, the symmetry index), the more similar the image pixels of two sides of the candidate section, that is, the symmetry index is better, thus the characteristic condition may be "symmetry index is the smallest". But for the symmetry index calculated by using the equation (28), the bigger the value of E (which means the value of E is closer to 1), the more similar the image pixels of two sides of the candidate section, that is, the symmetry index is better, thus the characteristic condition may be "symmetry index is closest to 1" or "symmetry index is the biggest".

When calculating the symmetry index according to other manners, the characteristic condition may be defined similarly. For example, when the symmetry index is the Euclidean Distance of the first region and second region, the characteristic condition may be "symmetry index is the smallest", that is, the smaller the symmetry index (that is, the smaller the Euclidean Distance), the better the symmetry of first region and second region; when the symmetry index is the Cosine Similarity Index of the first region and second region, the characteristic condition may be "symmetry index is the biggest", that is, the bigger the symmetry index (that is, the bigger the Cosine Similarity Index), the better the symmetry of first region and second region, etc.

As mentioned above, certain specific structures may be reflected in the median sagittal section image of fetus head, in other words, the median sagittal section image of fetus head contains certain unique structure characteristic. Therefore, in some other embodiments of the present disclosure, it may utilize this character of the median sagittal section image of fetus head to generate a template image (or standard reference image) of median sagittal section of fetus head, by using previously obtained images of the median sagittal section image of other fetus heads, after that, during the 3D imaging procedure, match the obtained sections in the 3D volume data with the template image, calculate the similarity index between the section in the 3D volume data and the target image, and the section which has the highest similarity index with the template image can be regarded as the median sagittal section image of fetus head.

Figure 18:
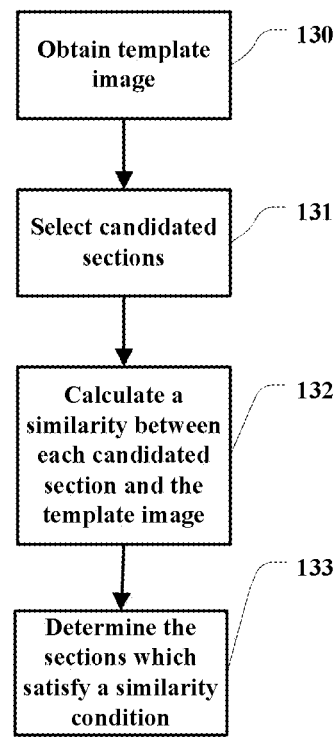
FIG. 18 is a schematic flow chart of a step of detecting the median sagittal section image according to still another embodiment of the present disclosure.

For example, in one embodiment of the present disclosure, a schematic flow chart of detecting the median sagittal section according to the 3D volume data is shown in FIG. 18.

In step 130, it may obtain a template image of the median sagittal section of fetus head. In one or more embodiments of the present disclosure, the template image may be generated according to previously obtained images of the median sagittal section image of other fetus heads and stored in a storage equipment in advance, and during the 3D imaging procedure of embodiments of the present disclosure, the template image may be directly read from the storage equipment, but it is also can be generated during the 3D imaging procedure of the present disclosure.

In the embodiments of the present disclosure, the template image may be one, or be more than one, for example, each of a plurality of templates may be used to match with sections having different sizes in 3D volume data.

When there are a plurality of template image, each of the candidate sections may be used to match with each of the template images.

After the template image is obtained, then in step 131, it may select a set of candidate sections in the 3D volume data. The selection manner of the candidate sections may be determined according to different needs, or the candidate sections may be selected according to certain previous knowledge, and candidate sections obviously do not containing the median sagittal section are discarded. For example, as the median sagittal section of fetus head is an vertical section located in middle position of the fetus head (that is, the sections along the direction from the top of the fetus head to the fetus neck), therefore according to approximate direction of the fetus image in the 3D volume data, it may select a set of vertical sections of the 3D volume data as the set of candidate sections. For example, it may select a set of vertical sections approximately located in the middle position of the head (such as all of the vertical sections apart at certain step-length or distance in specific region of the middle position of the head) as a set of candidate sections.

In the embodiments of the present disclosure, it may also select all of the sections apart at certain step-length in the 3D volume data, that is, to perform traversing matching to all the sections within all range of the 3D volume data by certain step-length and the template images.

For example, in one embodiment, when using Equation (21) to represent the section equation, if the value ranges or scopes of the plane parameters θ,φ,ρ are designated and the values of the step-length $\theta_{step},\varphi_{step},\rho_{step}$ are designated, then the selection of the candidate sections is realized.

Similarly, when using the general expression aX+bY+cZ+d=0 or Z=aX+bY+c or Y=aX+bZ+c to represent the section equation, if scopes of the plane parameters a, b, c and d are designated, and step-length of each is designated, then the selection of the candidate sections is realized.

For example, when all of the sections apart at certain step-length in the 3D volume data are selected as the candidate sections, the value range of the parameter ρ may be shown as equation (22), the maximum value range of θ,φ, for example, may be 0°≤θ<360° and −90°≤φ≤90° (refers to FIG. 14). It is easy to understand that, when the setting of the coordinates varies, value scopes of the parameters vary too.

The step-lengths $\theta_{step},\varphi_{step},\rho_{step}$ may be selected according to actual need of detection precision, and should not be limited by the present disclosure. For example, in one embodiment, it may be $\theta_{step}=1,\varphi_{step}=1,\rho_{step}=2$. It is easy to understand that, according to needed detection precision, the step-length also may be any other values.

Other detailed selection manner of the candidate sections may refer to aforementioned selection manner of candidate transverse section images, which will not be described herein again.

As mentioned above, in the embodiments of the present disclosure, there may be one single transverse section template image or one single template image. In this situation, the transverse section template image or the template image may be generated under a specific size. Thus, before selecting the candidate sections or candidate transverse section images from the 3D volume data, or before selecting a candidate transverse section image having the image characteristic as the transverse section to be measured from the image set of candidate transverse section images, or before calculating a similarity index between each candidate transverse section image of the candidate transverse section image set, it may include a step of aligning the 3D volume data with the transverse section template image or the template image, this step is to align the 3D volume data and the transverse section template image or the template image to the identical scale space, in other words, it makes the size of a structure in the 3D volume data and the size of a corresponding structure in the transverse section template image or the template image are approximate identical to each other. Or, it may also align each candidate transverse section image of the candidate transverse section image set and the transverse section template image to the same scale space. After being the alignment, each structure in the 3D volume data and each corresponding structure in the template image have the same size, thus the subsequent matching procedure may be easier to implement, the matching result may be better, and may reduce the amount of calculation of the matching procedure.

A method of aligning the 3D volume data or each candidate transverse section image of the candidate transverse section image set with the transverse section template image or the template image, may include detecting object of interest (for example, the skull halo) of the transverse section image in the candidate transverse section image set or the 3D volume data (for example, it may select the image of the middlemost frame, that is, the image of F/2 frame, or may select the image of a neighboring frame or other frames, or other section images). After that, transforms the 3D volume data to a scale level identical to the size of the template image according to the size of detected object of interest by way of rotating, offsetting and/or zooming.

Herein, transforming the 3D volume data or each candidate transverse section image of the candidate transverse section image set to a scale level identical to the size of the transverse section template image or the template image refers to, cause the structure of the 3D volume data or the candidate transverse section image and the same or corresponding structure of the transverse section template image or the template image have the same size.

Herein, the "same" refers to basically or approximately identical or similar, and should not be strictly limited to absolutely identical, but a certain difference or error may be allowed. In other words, the "same" should not be explained strictly and idealistically.

In the embodiments of the present disclosure, any other suitable method may be used to align the 3D volume data and the transverse section template image or the template image to the identical scale space.

Herein, the "identical" refers to basically or approximately identical or similar, and should not be strictly limited to absolutely identical, but a certain difference or error may be allowed. In other words, the "identical" should not be explained strictly and idealistically.

After designating the candidate sections, in step 121, it may perform the traversing search, by the selected step-length, to equations $\rho,\theta,\varphi$ of all the candidate sections within value scope of the plane parameter, and match each of the candidate sections and the template image. For example, it may calculate the symmetry index between each candidate section and the template image.

The similarity index is used to measure the similarity between the candidate section and the template image. In the embodiments of the present disclosure, the similarity index may be calculated according to various manners, and details can be referred to aforementioned calculation of the similarity index between the candidate transverse section image and the transverse section template image, which will not be described herein again.

For all of the candidate sections, a similarity index of each candidate section is calculated to obtain a set of similarity indexes. After that, select one or more characteristic similarity indexes satisfy the characteristic condition from the set of similarity indexes, in one or more embodiments of the present disclosure, the candidate section corresponding to the characteristic similarity index can be regarded as a needed median sagittal section image of fetus head. Herein, the "characteristic condition" may be a condition indicating the similarity of a candidate section is optimum. The characteristic condition may vary according to different similarity index calculating methods, which can be referred to aforementioned descriptions related to the "image characteristic condition" and will not be described herein again.

In one embodiment of the present disclosure, in step S30, it may display the transverse section on a display. Or, based on contents of aforementioned step S20, it may replace the "transverse section" with the "coronal section" to obtain a technical solution of detecting, from the 3D volume data, a coronal section at an anatomical position according to image characteristic of the head of the target body in the coronal section related to the anatomical position. Similarly, based on contents of aforementioned step S20, it may replace the "transverse section" with the "sagittal section" to obtain a technical solution of detecting, from the 3D volume data, a sagittal section at an anatomical position according to image characteristic of the head of the target body in the sagittal section related to the anatomical position.

No matter which type of section relates to anatomical position is being detected, they all can be obtained base on the technical solution of the step S20, and only have to replace the "transverse section" with the name of a corresponding section, thus procedures similar to step S20 for automatically detecting each type of section will not be described in detail, and may refer to related descriptions mentioned above. In addition, because of the structural particularity of the sagittal section, when detecting a sagittal section, it may also refer to aforementioned descriptions relate to embodiments of "detecting the median sagittal section image from the 3D volume data".

Therefore, in step S30, it may also show the sections at the anatomical positions detected from the 3D volume data on the display, and all of these sections may be detected from the 3D volume data, according to image characteristic of the head of the target body in the section related to the anatomical position, based on the step S20.

Figure 21:
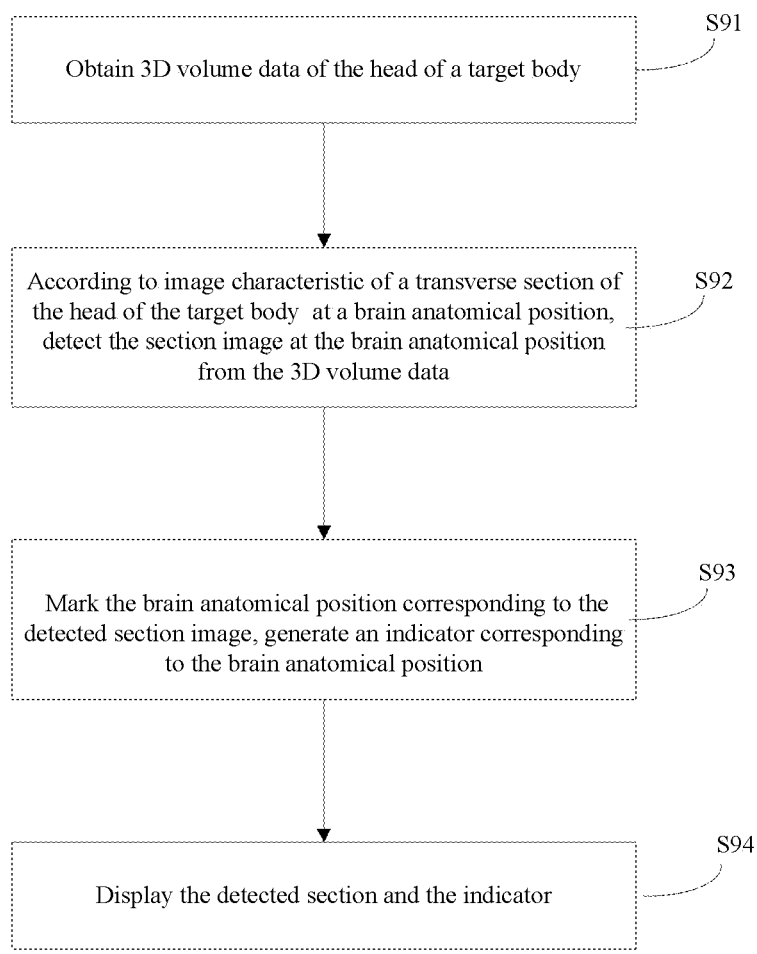
FIG. 21 is a schematic flow chart of a method according to one of the embodiments of the present disclosure.

In order to highlight the relationship between the section and the anatomical position, as shown in FIG. 21, in one embodiment, after performing the step S92 of detecting the section at the anatomical position from the 3D volume data obtained through the step S91, according to image characteristic of the head of the target body in the section related to the anatomical position, it may further include the following steps of step S93 and step S94. The detailed implementation process related to step S92 may be referred to aforementioned descriptions related to step S20 and step S11, detailed implementation process related to step S91 may be referred to aforementioned descriptions related to step S10, which will not be described herein again.

In one embodiment, in step S93, it may mark the anatomical position corresponding to the detected section, and generate an indicator corresponding to the anatomical position. In step S94, it may display the detected section and the indicator by utilizing the display.

For example, in one embodiment, it may mark the anatomical position corresponding to the detected section in a section schematic and generate the indicator; and display the section schematic and the detected section in comparison, and display the indicator in the section schematic (or section structure image) in step S94.

The mentioned herein may include at least one section schematic of three types of section including the brain sagittal section, the coronal section, and the transverse section, or it may include the schematic diagram of any section of the head of the target body. Certainly, for showing the aforementioned anatomical position corresponding to the detected section more clearly, it may select an appropriate section schematic according to the need. For example, if to mark the median sagittal section image, the section schematic shown in FIG. 4 may be utilized; or may as shown in FIG. 22, if a transverse section is to be marked, thus can mark the anatomical position corresponding to the transverse section detected in step S92, on the structure schematic diagram of the median sagittal section image (as shown in the upper left of FIG. 22) and generate a corresponding indicator; in step S94, display the section schematic of the median sagittal section image and the transverse section in comparison, and display the indicator in the section schematic of the median sagittal section image.

Figure 19:
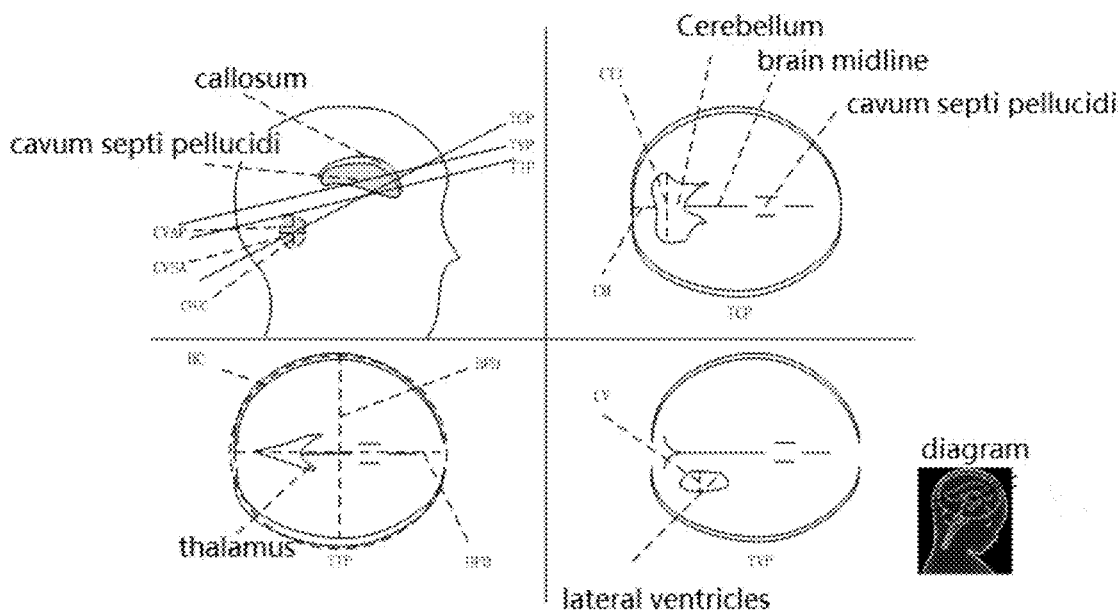
FIG. 19 is a display effect schematic diagram of a display interface of a display according to one embodiment of the present disclosure.

For another example, in another embodiment of the present disclosure, it may include: marking, in at least one type of section selected from three types of section including brain sagittal section, coronal section and transverse section of the 3D volume data, the anatomical position corresponding to other types of section of the three types of section, and generating the corresponding indicator; and in step S94, displaying the at least one type of section and the other types of sections in comparison, and displaying the indicator in the at least one type of section. As shown in FIG. 19, the brain sagittal section detected from the 3D volume data which is shown in upper left may be displayed in comparison with the transverse section, and the anatomical position corresponding to the transverse section may be marked in the brain sagittal section. For another example, the brain sagittal section shown in upper left of FIG. 19 may be replaced by a brain coronal section, thus the anatomical position corresponding to the transverse section may be marked in the brain coronal section. In one embodiment of the present disclosure, as shown in FIG. 19, on the median sagittal section image of the sections detected in step S92, it can mark the anatomical position corresponding to the transverse section detected in step S92 and generate a corresponding indicator; and then in step S94, display the median sagittal section image and the transverse section in comparison, and display the indicator on the median sagittal section image.

In step S93 of the present embodiment, it may mark the anatomical position corresponding to the detected section, by a manner of marking the anatomical position corresponding to certain section on a reference image. The reference image refers to an image carrier on which an indicator is drawn, and may be selected from section schematics for characterizing brain sagittal section, coronal section and/or transverse section, or from sections of brain sagittal section, coronal section and/or transverse section in the 3D volume data. For example, it may characterize the anatomical position corresponding to the section by utilizing an intersection line between the section and a section shown by the reference image. In one embodiment of the present disclosure, in aforementioned step S93, it may generate the indicator by marking the intersection line. The anatomical position corresponding to one section may be represented by an indicator corresponding to one intersection line. Such as, generates an indicator for marking the anatomical position corresponding to the transverse section by marking the intersection line of the median sagittal section image and the transverse section.

Figure 22:
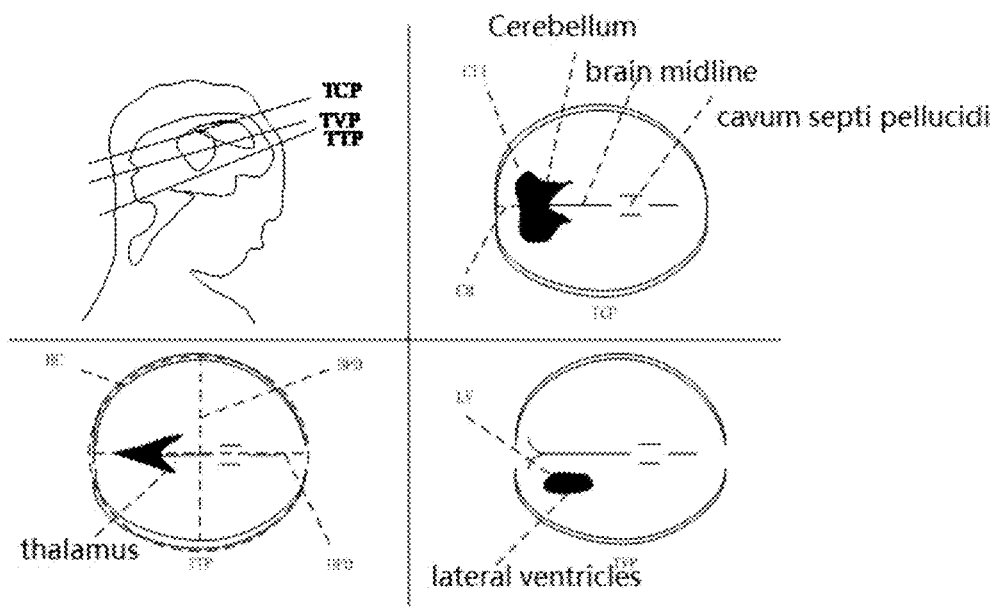
FIG. 22 is a comparison display effect diagram of a section schematic and a transverse section image according to one embodiment of the present disclosure.

As shown in FIG. 19 and FIG. 22, it may use a reference line added at the corresponding anatomical position for expression, such as the straight lines relates to TCP, TTP, and TVP. The reference lines drawn in FIG. 19 and FIG. 22 may be regarded as indicators for expressing the intersection lines. The color of these reference lines may be adjusted according to the user's need, thus by different colors may be used to differentially express marked different transverse sections, in other words, at least one section, detected from the 3D volume data according to image characteristic of the head of the target body in a section related to at least one anatomical position, may be expressed by using reference lines with different colors. It may also, in the display window of the corresponding transverse section, use characters or other indicators with the corresponding color to show the name of the transverse section. For example, use "TCP" in upper right diagram of FIG. 19 to represent the cerebellum section, use "TVP" in lower right diagram to represent the lateral ventricle section, use "TTP" in lower left diagram to represent the thalamus section, and the display region of the upper left diagram is used for displaying the median sagittal section image. The FIG. 19 shows an embodiment of displaying according to the present disclosure. The median sagittal section image and the three standard sections of lateral ventricle section, thalamus section and cerebellum section may be displayed on one single interface of a display device, and may mark anatomical positions corresponding to the three standard sections of lateral ventricle section, thalamus section and cerebellum section, in the median sagittal section image by utilizing reference lines with different colors or different line types. The length of the reference lines may be set according to actual needs.

Figure 23:
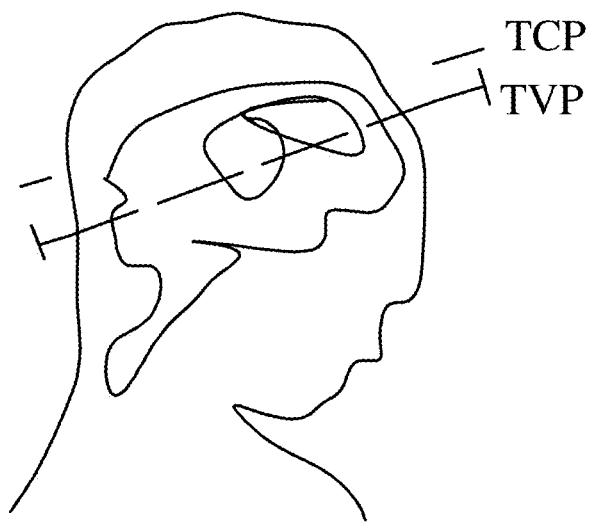
FIG. 23 is a schematic diagram of marking a intersection line on the section schematic according to one embodiment of the present disclosure.

Both of FIG. 19 and FIG. 22 draw reference lines to generate the indicator for marking the intersection lines. Certainly, the manner of expressing the intersection line is not limited to the reference line, for example, it may be: non-continuous line segments, such as a profile position indicator line in mechanical drawing. For example, FIG. 23 cut two line segments at two ends of the reference line for expressing, and may further use thickness or color of the line segment for distinguishing. Or, it may also be: marking two corresponding symbols such as "⊥", "┌", or "┘" at corresponding anatomical position outside of the skull halo, to replace the reference line. Or it may be as shown in FIG. 23, shows the position of the marked section by using symbol labels (e.g. the TCP, TTP, or TVP), when moving the mouse to the symbol labels or related section image, converts the attribute of the indicator for marking the reference line or the indicator corresponding to the section from invisible to visible. Such as, when the mouse pointing to the symbol label of TVP in the schematic diagram of the sagittal section structures shown in FIG. 23, the middle dash line changes from invisible to visible, thus the user can see the indicator of the anatomical position, and also avoid to lower the display image quality due to too many indicators for marking the sections (the definition of the attribute of visible and invisible in the following description can be referred to above description). Therefore, in some embodiments of the present disclosure, configure the indicators for marking the intersection line or anatomical position with different parameters and/or attributes to identify different marked sections, the parameter and/or attribute include: any of color of the indicator, shape of the indicator (e.g. the various kinds of line types of the reference line, including dash lines, solid lines, and dot dash lines in the FIG. 19), symbol label, indication label (including by way of marking a guide line and a note symbol), proportion of the indicator, and visibility of the indicator, and any combination thereof. The present disclosure includes but not limits the setting of aforementioned indicator parameter or attribute, as long as it is an indicator for marking the intersection line between the section and the section shown in the reference image to characterize the corresponding anatomical position, it should be applied to one or more embodiments of the present disclosure.

In the aforementioned step S92, it may include allowing the user manually rotate or offset the sections (includes sagittal sections, e.g. the median sagittal section image) to change the position of the section, or changing the anatomical position by adjusting the indicator, or allowing the user choose the reference image, through man-machine interaction manners such as keys, promotion boxes, trackballs or widgets configured on the display for receiving user input instructions. For example, in FIG. 19 and FIG. 22, it allows the user manually change the position of the reference lines TCP, TTP, and TVP to modify the displayed image of the transverse section (e.g. the cerebellum section, the thalamus section and the lateral ventricle section).

For example, in one aspect, the step S93 includes the following steps:

Firstly, get a selection instruction of selecting a reference image by a user, definition of the reference image can be seen in aforementioned descriptions;

After that, mark the anatomical position corresponding to the detected section in the reference image according to the selection instruction. The present embodiment gives the user certain selectivity, and provides more friendly user interface.

In another aspect, it provides the user certain selectivity for the indicator, and provides more friendly image display effect. In another embodiment of the present disclosure, the step S93 includes the following steps:

Firstly, receive a signal generated from a user selecting the indicator or at least a section. The selecting of the indicator or at least a section includes selecting the indicator or the section in the display interface by utilizing a man-machine interaction manner; or it may include, moving, through a man-machine interaction manner, at a certain speed the indicator or the section at the position of the cursor in the display interface.

After that, converts the attribute of the indicator from invisible to visible, or converts the attribute of the indicator generated for marking the anatomical position corresponding to the at least one section from invisible to visible, according to the generated selection signal.

Figure 24:
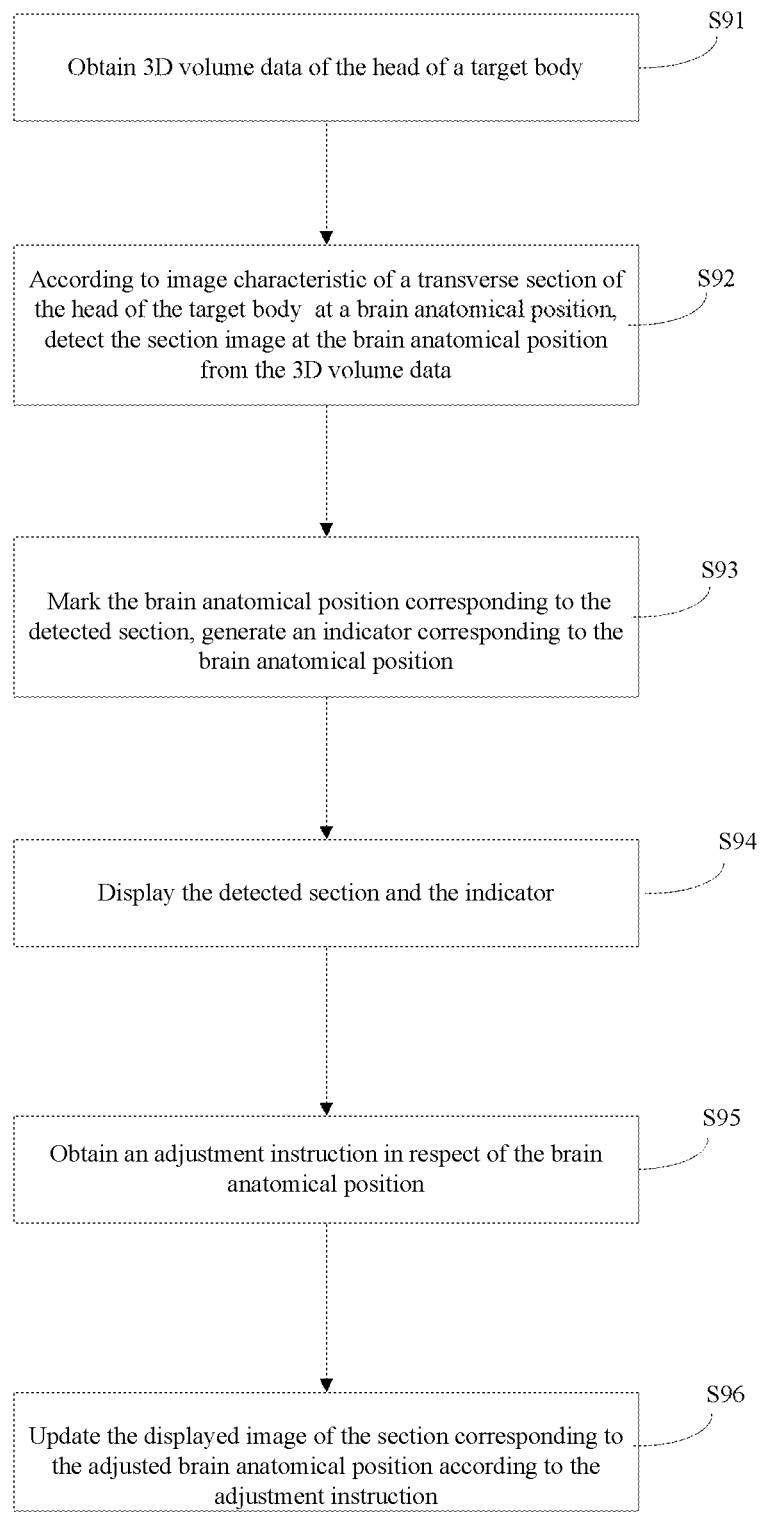
FIG. 24 is a schematic flow chart of a method according to one of the embodiments of the present disclosure.

For another example, in one embodiment of the present disclosure as shown in FIG. 24, the aforementioned method may include the following steps:

Step S95, obtaining an adjustment instruction in respect of the anatomical position. For example, based on the displayed reference image, the user may adjust the marked anatomical position in the reference image by utilizing a man-machine interaction manner.

Step S96, updating the displayed image of the section corresponding to the adjusted anatomical position according to the adjustment instruction. As shown in FIG. 19, when the user adjusting the position of the reference lines related to the TCP, TTP, or TVP in the upper left diagram by utilizing a man-machine interaction manner, a corresponding adjustment instruction is produced or generated. According to variation information in the corresponding adjustment instruction, adjusts the display image of the other three diagrams in the FIG. 19. in other words, extracts image data of the section corresponding to the adjusted anatomical position according to the adjustment instruction. In one embodiment of the present disclosure, it may include, extracting sections from the 3D volume data by utilizing the adjusted anatomical position, displaying the extracted sections as the updated display image.

Figure 25:
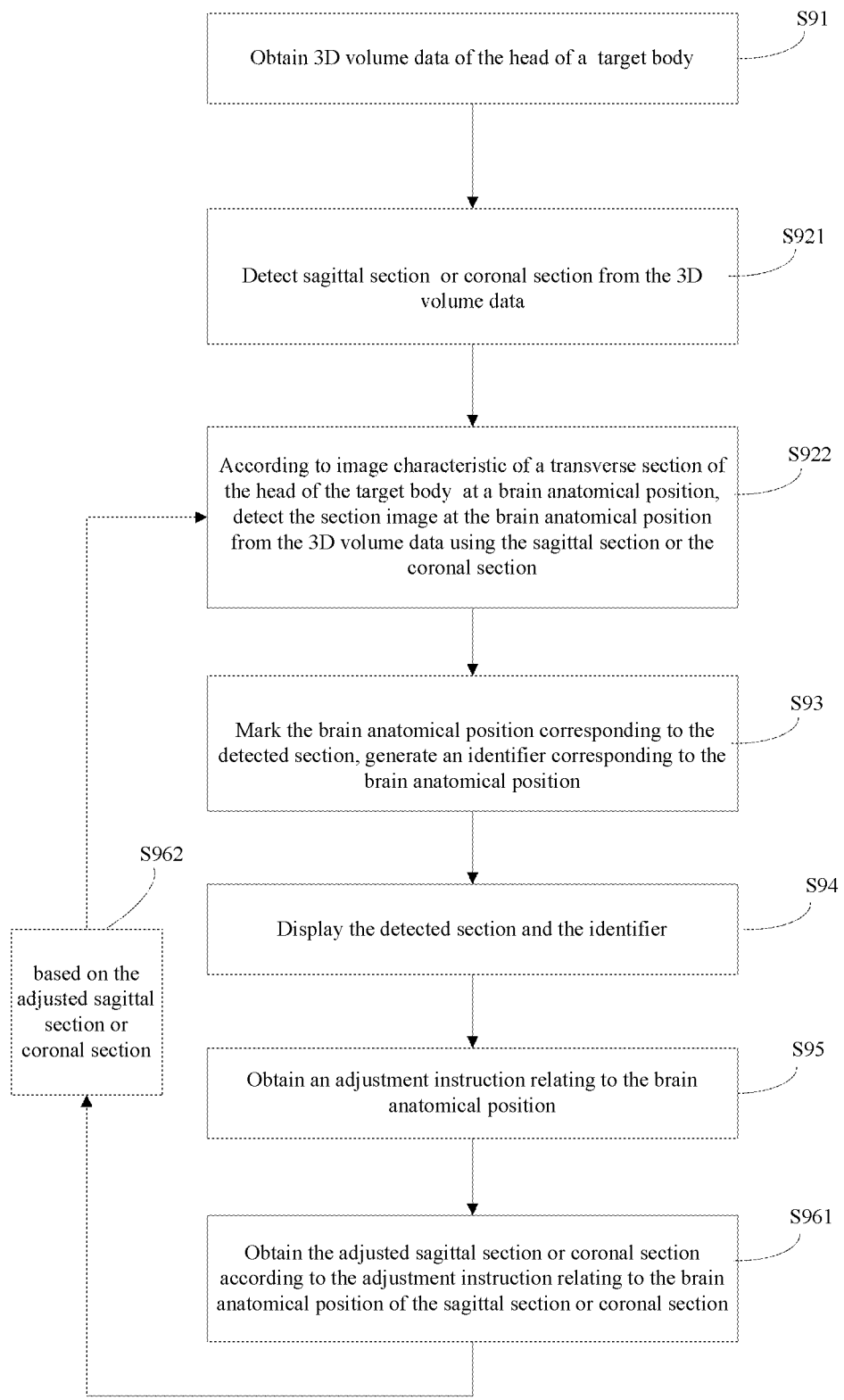
FIG. 25 is a schematic flow chart of a method according to one of the embodiments of the present disclosure.

In this embodiment, it allows the user manually calibrate the error of automatically detecting images, to make obtaining of the images more accurate, thus to provide the practitioners more accurate image display data. Based on this, when aforementioned method needs to detect the transverse section at the anatomical position from the 3D volume data by utilizing a sagittal section or a coronal section, such as in the step S12 and step S20, then as shown in FIG. 25, the step S92 may include:

Step S921, detecting a sagittal section or coronary section in the 3D volume data;

Step S922, detecting a transverse section at the anatomical position from the 3D volume data by utilizing the sagittal section or coronary section according to image characteristic of the head of the target body in a transverse section related to the anatomical position (can be referred to related descriptions of step S21); and the step S96 includes:

Step S961, according to the adjustment instruction in respect of the sagittal section or coronary section of anatomical position to obtain adjusted sagittal section or coronary section;

Step S962, returning to the step S922 based on the adjusted sagittal section and coronary section, to re-detect the transverse section at the anatomical position from the 3D volume data;

Step S94, displaying the adjusted sagittal section or coronary section, and the re-detected transverse section. Therefore, in one embodiment of the present disclosure, receives a user's adjustment instruction for adjusting the median sagittal section image, obtain an adjusted median sagittal section image according to the adjustment instruction, and detects the transverse section to be detected from the 3D volume data by utilizing the adjusted median sagittal section image according to image characteristic of the head of the target body in the transverse section related to the anatomical position.

In the aforementioned embodiments, besides adjusting the displayed median sagittal section image, it may also adjust the displayed transverse section. In one embodiment of the present disclosure, a method of manually modify the sagittal section or transverse section is provided, which may include:

Firstly, according to an activation signal of the display window, receiving adjustment instruction input by the user through the widget, the button, the promotion box, or the trackball;

After that, analyzing the adjustment instruction to obtain operation type and amount of adjustment, the operation type includes offsetting or rotating the image;

Next, according to the operation type and amount of adjustment, performing operation corresponding to the operation type to the section image in the activated display window or the indicator for marking the corresponding anatomical position of the section, and displaying corresponding to the section image after operation. The marking relates to the anatomical position of the adjusted section changes correspondingly. For example, in one embodiment of the present disclosure, it may further include: according to the updated displayed section image of aforementioned step S96, to re-determine the marked anatomical position in the section image. When there is display indicator in the section image, when the section image updates, the indicator updates correspondingly.

The present embodiment may be applied to aforementioned obtaining of adjustment instruction of adjusting median sagittal section image by the user and obtaining adjusted median sagittal section image according to the adjustment instruction, and may be applied to aforementioned obtaining of adjustment instruction of adjusting transverse section by the user and obtaining adjusted transverse section according to the adjustment instruction. Or, it may also be applied to embodiments of executing operations after obtaining adjustment instruction relates to anatomical position based on reference image.

For example, after the sagittal section (such as the median sagittal section image) is automatically detected and displayed in a sagittal section display window, the user may activate the sagittal section display window to receive adjustment instructions, such as offsetting or rotation input by the user through the widget, the button, the promotion box, or the trackball. If use the trackball to perform offsetting, it may use X, Y, or Z rotation key to perform rotation of corresponding direction respectively. According to the adjustment instruction, obtains an adjusted median sagittal section image, and further based on the adjusted median sagittal section image, recall the automatic detection algorithm of transverse section in step S20, and recalculate the transverse section for displaying.

In another embodiment of the present disclosure, the user may move the trackball or other man-machine interaction equipment to the corresponding reference line of the transverse section to be modified, and then activate the reference line by clicking the trackball singly. After been activated, the reference line may be colored by using different colors or lined in different line types (dash line or solid line) based on the user's selection, to represent the activated state. At this time, offsetting or rotating the reference line by utilizing such man-machine interaction equipment or interface widget as trackball, rotary knob, and menu keys. As the reference line and the corresponding transverse section have an interactive relationship, so the corresponding transverse section will change correspondingly. Or, the user may activate a certain standard transverse section window, after that, may offset or rotate the reference line by utilizing such man-machine interaction equipment or interface widget as trackball, rotary knob, and menu keys, at this time, the reference line of the corresponding transverse section needs to be offset and rotated correspondingly.

In the embodiments described above, when displaying of the schematic diagram of the section structures and the detected section for comparison, or displaying of at least two of the brain sagittal section, the coronal section, and the transverse section of the 3D volume data for comparison, a new image displaying manner is also provided, and base on this manner, it may show information of related target tissue at various positions. Thus, one embodiment of the present disclosure may further include:

Firstly, it may obtain the marked initial position and terminal position on the aforementioned reference image. For example, it may obtain marked initial position and terminal position on the median sagittal section image (such as the upper left of FIG. 19) or the schematic diagram of the section structure (such as the small diagram at the lower right of FIG. 19). The initial position and the terminal position may be the anatomical position characterized by indicator such as aforementioned intersection line according to the user's input, or may be determined according to a plurality of candidate transverse section images (when using aforementioned step S20 to detect a section, such as a transverse section to be tested, a sagittal section to be tested, or a coronal section to be tested, it should be replaced with a plurality of candidate sections) obtained in step S24 when selecting at least one similarity index from a set of similarity indexes satisfying the image characteristic, for example, in the aforementioned 3D volume data, all of the candidate transverse section images corresponding to the selected similarity index are included between the initial position and the terminal position.

Next, replaying a plurality of parallel sections starting from the initial position to the terminal position sequentially. For example, replaying a plurality of parallel transverse sections which are vertical to the median sagittal section image, starting from the initial position to the terminal position sequentially. As shown in FIG. 8a, the initial position or the terminal position can be a corresponding anatomical position of section 103 and section 104 in the median sagittal section image or the structure schematic diagram of the head of the target body. Thus according to aforementioned method, after determining the initial position and the terminal position, replaying the parallel transverse sections which are vertical to the median sagittal section image between the initial position to the terminal position sequentially and automatically on the interface of the display. Therefore it can sufficiently show the user the complete section vision of the 3D stereoscopic structure of the target tissue selected scope, and completely show the user or the practitioner lesion or growth situation of the target tissue, which may promote the usage experience of the present disclosure. In addition, it may show all of the automatic detected candidate transverse section images according to step S24, and further select the candidate transverse section image with more accurate position as the ultimate transverse section to be tested according to user experience. When the user determines to extract a specific transverse section, he or she can enter such instruction information as suspending the replay or display, or extracting the transverse section being replayed through such man-machine interaction manner as keys, and the current transverse section is kept on the display based on the instruction information, or extracting the current transverse section and save it, or saving the anatomical position corresponding to the displayed transverse section. In this disclosure, for information storage and/or display, the data needs to be stored or saved for marking or recording the anatomical position, or generating the indicator to mark the anatomical position include at least: position information on the reference image, or further the parameter and/or attribute of the indicator. Or, it may determine the correct anatomical position of the transverse section according to the current displayed transverse section and record it for marking. Therefore, in one embodiment of the present disclosure, the step S93 may also include recording and saving the position information of the corresponding indicator on the reference image, and/or the parameter and/or attribute of the indicator.

In addition, the plurality of parallel sections starting from the initial position to the terminal position can be displayed in comparison manner on the display. The display manner in comparison may be shown as in FIG. 19 and FIG. 22, which is, displaying on one display interface a plurality of images. Similarly, when displaying in comparison, all of the sections automatically detected according to the step S24 may be simultaneously displayed or scrolling displayed on the same display interface.

Figure 27:
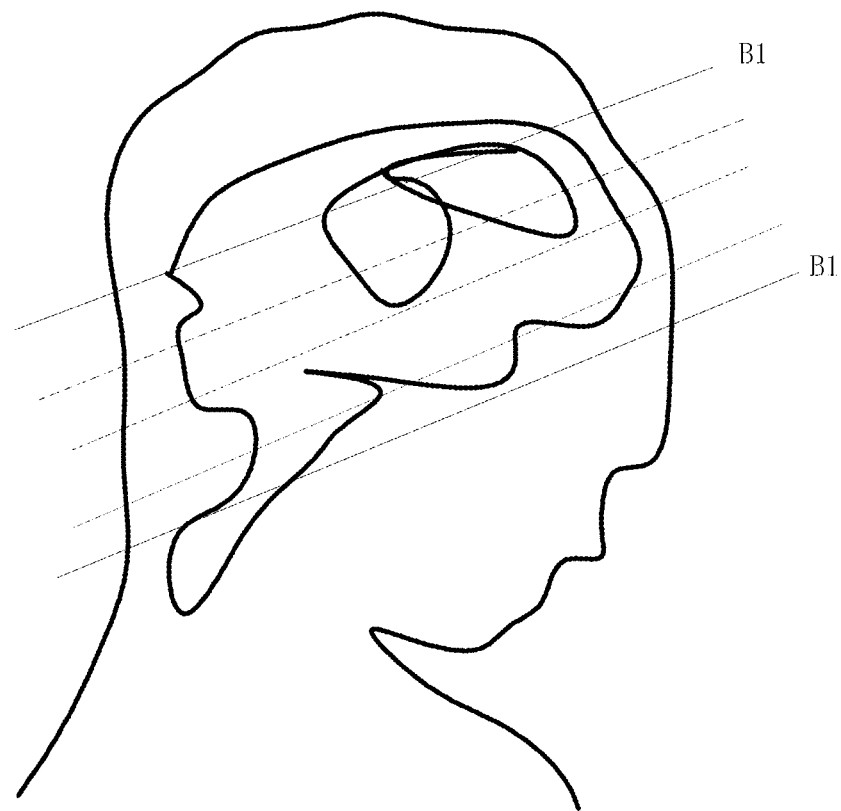
FIG. 27 is a display effect diagram of showing an indicator according to one embodiment of the present disclosure.

For distinguishing the different sections sequentially replayed or displayed in comparison, marking the anatomical position corresponding to the current displayed section by utilizing an indicator moving between the initial position and the terminal position, in other words, when sequentially replaying or displaying in comparison, sequentially replaying the indicators for marking the anatomical positions corresponding to the plurality of parallel sections, synchronously. For example, as shown in FIG. 27, when marking the initial position B1 and the terminal position B2 in the schematic diagram of the section structures, using a plurality of dash lines between two solid lines representing the initial position B1 and the terminal position B2 to characterize a plurality of corresponding anatomical positions of a plurality of parallel sections there between respectively, and the different scales of the dash lines may represent the different time of visualization, such that the user may see a moving indicator. Certainly, the indicator includes but not limited to the line segment shown in FIG. 27 of this embodiment, which may be seen aforementioned descriptions related to the indicator, and will not be described herein again.

Certainly, when sequentially replaying or displaying in comparison, at the same time, it may mark the anatomical positions corresponding to a plurality of parallel sections by setting different parameters of the indicators, which can be referenced to aforementioned related descriptions and will not be described herein again.

Figure 26:
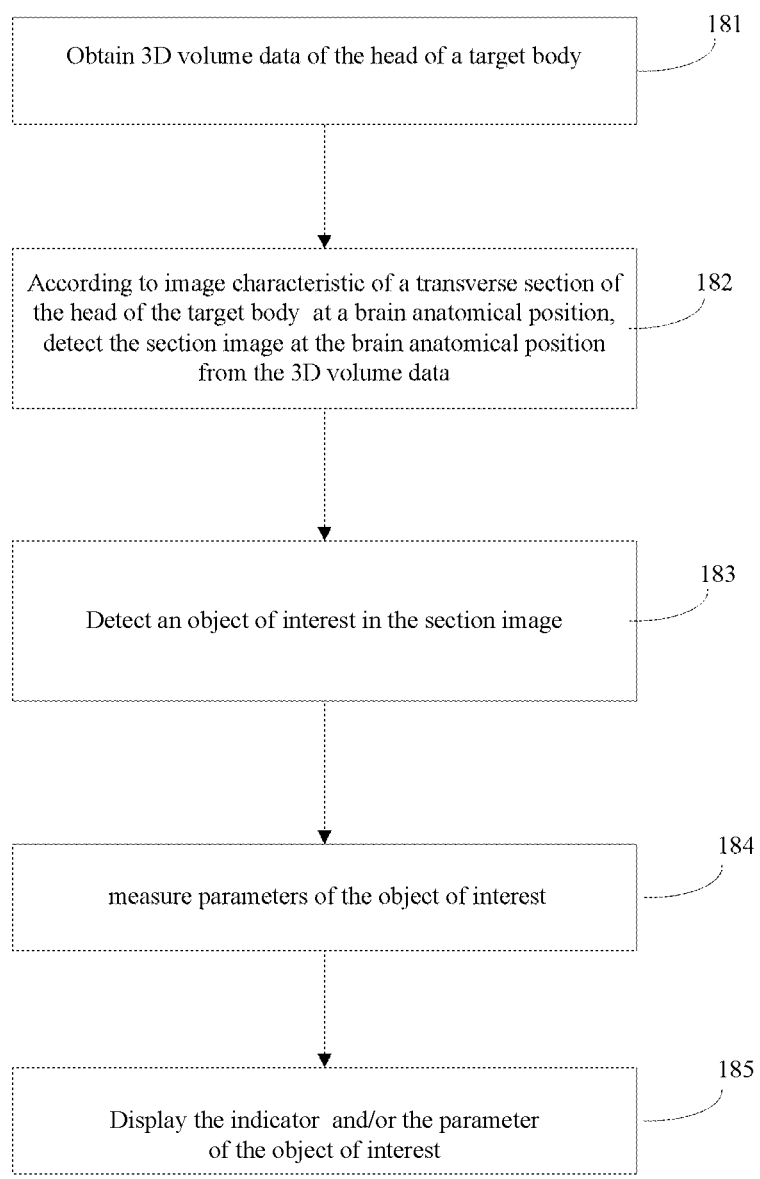
FIG. 26 is a schematic flow chart of a method according to one of the embodiments of the present disclosure.

Based on aforementioned embodiments, the present disclosure also provides a display method of automatically measuring and displaying structure parameters of related target tissue, which may be shown as in FIG. 26. The object of interest mentioned in this embodiment may include some important anatomical structures expected to be automatically measured in the standard sections, for example, the skull halo, the thalamus, the cerebellum and the lateral ventricle, etc. The parameters of the object of interests may include such frequently-used measure items marked by dash lines as shown in FIG. 19. For example, the parameters measured automatically may include: biparietal diameter (BPD), occipito-frontal diameter (OFD), and/or head circumference (HC) in the thalamus section; transverse diameter of the cerebellum (CTI), and/or posterior cranial fossa width (CM) in the cerebellum section; lateral ventricle width (LV) in the lateral ventricle section; cauda cerebella anteroposterior diameter (CVAP), cauda cerebella uperoinferior diameter (CVCC) and cauda cerebella area (CVSA), etc. in the sagittal section, etc.

In step 181 of the present embodiment, obtaining the 3D volume data of the head of the target body; details can be seen related specification in aforementioned step S10, which will not be described herein again.

In step 182 of the present embodiment, detecting, from the 3D volume data, a section at an anatomical position according to image characteristic of the head of the target body in a section related to the anatomical position; details can be seen related specification in aforementioned step S92, which will not be described herein again.

In step 182 of the present embodiment, detecting an object of interest in the section. According to shape characteristic of the object of interest, fitting the region of interest in the section by utilizing a model matches the shape characteristic or other characteristic of the object of interest to obtain the object of interest. For example, fitting the region of interest detected in transverse section of the sections by utilizing an ellipse model to obtain the maximum ellipse for characterizing the skull halo region. Fitting the segmented ROI of cauda cerebella by utilizing an ellipse model, to obtain a measurement region of cauda cerebella.

In one embodiment of the present disclosure, step 183 may include: detecting the object of interest in a median sagittal section image and/or transverse section, wherein the transverse section comprises at least one of thalamus section, cerebellum section and lateral ventricles section. The median sagittal section image and/or the transverse section may be obtained by detecting according to step 182, which can be seen above.

In step 185 of the present embodiment, marks the object of interest and/or the structure parameter in the section where the specific structure characteristic is existed, and then displays it. It may also display the object of interest and/or the structure parameter. For example, as shown in FIG. 19 and FIG. 22, drawing the detected ellipse in step 183 in the thalamus section, the cerebellum section and the lateral ventricle section respectively, and drawing ellipse in the thalamus section, the cerebellum section and the lateral ventricle section for marking the skull halo region. Or, expresses the boundary of the specific structure characteristic of the segmented thalamus or cerebellum by using lines.

In addition, meaning of the corresponding structure parameters may be marked by line segments, for example, the line segments shown in FIG. 19 and FIG. 22 represent meaning of distance of measured BPD and OFD, etc. in step 184, thus to mark the structure parameter.

In one embodiment of the present disclosure, it may adopt the manner of drawing boundary of the object of interest to mark the object of interest, and also may use different colors or line types to draw boundary of the object of interest so as to distinguish them.

In one embodiment of the present disclosure, when marking the structure parameter, it may use different indicators to express different structure parameters, for example, line segment may represent distance parameter, colored curve represents head circumference, different colored blocks represent areas, or it may use the manner of symbol marking to remark the related structure parameter on the display interface. In addition, for using different indicators to distinguish different structure parameters, in another embodiment of the present disclosure, the step 185 may further include:

Firstly, obtaining the object of interest selected by the user to generate the selection signal. The meaning of selecting the object of interest may be seen in aforementioned descriptions, which may include selecting the object of interest by way of clicking in the display interface through man-machine interaction manner; or it may include, through man-machine interaction manner, moving at a certain speed the object of interest at the position of the cursor in the display interface.

After that, according to the selection signal, converting the attribute of the indicator for marking the corresponding structure parameter of the object of interest from invisible to visible. The indicator for marking the corresponding structure parameter of the object of interest may include: aforementioned line segments, colored blocks, colored curves, guide lines, symbol marks (for example, name or value of the related structure parameter marked by utilizing characters or digitals), or any combinations thereof.

In the aforementioned step 185, it may include but not limited to aforementioned marking manners or indicator types. It can also reference the aforementioned related marking manners, or may use any other marking manner which can highlight the object of interest in the displayed image and exhibit the structure parameter in the displayed image, which can be implemented in various embodiments of the present disclosure.

The aforementioned step 183 to step 185 will be described in details along with examples of automatically detecting and displaying structure parameters of related target tissue of the transverse section and/or the median sagittal section image, respectively.

The automatic measurement of HO, BPD and OFD are mainly performed on the thalamus section. The step 183 to step 185 can be implemented as the following Step 411 to Step 413 respectively, and may include the following steps in detail:

Step 411: fitting the region of interest detected from the thalamus section obtained according to aforementioned step S10-S20 by utilizing ellipse, and drawing a maximum ellipse in the thalamus section for characterizing the skull halo. In the present embodiment, the skull halo is characterized by the drawn ellipse. The head circumference (HO) utilizes ellipse to perform envelopment to the outside of the skull halo, and the skull halo appears to be highlighted echo. The aforementioned Hough transformation, radon Hough transformation, radon energy optimization, Radon transformation, and/or least square estimation method, etc. may be used to perform the ellipse fitting. The ellipse equation may adopt the standard common equation:

$$x^2 + ay^2 + bz^2 + cxy + dyz + exz + f = 0$$

As the transverse sections are all vertical to the sagittal sections, thus the rotation angle of the ellipse of the transverse section may be regarded as 0°. Therefore, during the detection, it may adopt the standard ellipse equation:

$$\frac{(x - x_0)^2}{a^2} + \frac{(y - y_0)^2}{b^2} = 1$$

After the ellipse equation is obtained, it may draw the ellipse in the thalamus section image, and calculate the ellipse circumference and further calculate pregnancy week of fetus according to the circumference.

Based on aforementioned methods, in one embodiment of the present disclosure one, fitting the region of interest detected from the transverse section by using an ellipse model and drawing maximum ellipse in the displayed transverse section to characterize the skull halo. The ellipse represents the skull halo.

Step 412: measuring circumference of the ellipse to characterize the head circumference (HO), measuring the short axis of the ellipse or distance between two neighboring points of the two ends of the short axis to characterize the biparietal diameter (BPD), and/or long axis of the ellipse or distance between two neighboring points of the two ends of the long axis to characterize the occipito-frontal diameter (OFD).

The biparietal diameter (BPD) is described by a distance between two points in clinical, wherein a near field point is located in outside of the skull halo, and a far field point is located in inside of the skull halo (as the BPD shown in left bottom of FIG. 19). It may use the short axis of the ellipse of the HO to describe the BPD. Or, it may use the distance between two neighboring points of the two ends of the short axis to describe the BPD, wherein a first point can directly adopt one end of the short axis of the ellipse, or searches along the upward direction near the upper end of the short axis of the ellipse a point with most brightness decrease to be the upper end of the BPD. Similarly, searches along the upward direction near the lower end of the short axis of the ellipse a point with most brightness decrease to be the lower end of the BPD. Similarly, neighboring point of the long axis refers to the point with most brightness decrease from left to right near one end of the long axis. So it can be seen that, the neighboring points or points at the neighboring position refers to the points with most brightness decrease along the direction of the short axis or long axis near the corresponding ends of the short axis or long axis.

The occipito-frontal diameter (OFD) also can directly use two ends of the long axis of the ellipse in the HC as two ends of the OFD.

Step 413: marking the head circumference (HC), the biparietal diameter (BPD), and/or the occipito-frontal diameter (OFD) in the thalamus section.

The automatic measurement of CTI and CM is mainly performed on the cerebellum section. The step 183 to step 185 can be implemented as the following Step 421 to Step 423 respectively, and may include the following steps in detail:

Step 421: fitting the region of interest detected from the cerebellum section obtained according to aforementioned step S10-S20 by utilizing ellipse, and drawing a maximum ellipse in the cerebellum section for characterizing the skull halo, by using aforementioned manner of Step 411.

According to a priori position, setting one searching region ROI or searching in the ellipse region, detecting upper and lower boundary of the cerebellum according to cerebellum boundary characteristic, obtaining the cerebellum boundary by using segmentation, marking and displaying the same; for example, the searching region ROI may be low-echo region in the ellipse or non-low-echo.

Figure 20:
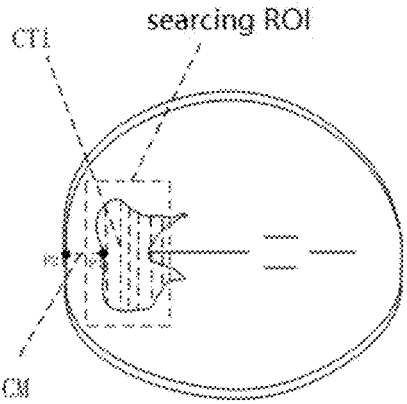
FIG. 20 is a display effect diagram of an automatic measurement of the cerebellum section image.

Step 422: selecting two points with the widest vertical distance (vertical direction) in the cerebellum boundary as two ends of the CTI, measuring the distance between the two ends to characterize the transverse diameter of the cerebellum (CTI). The posterior cranial fossa (CM) is constructed by liquid and appears as low-echo in ultrasonic image, but on the long axis of ellipse the cerebellum side appears as low-echo, thus the boundary of the posterior cranial fossa is obvious. A method of automatic measuring CM may be: searching, starts at an arbitrary point along the long axis of the ellipse (which can be set according to priori position), from center to outside of the ellipse, a point or region with most gray scale decrease as the first point (as P1 shown in FIG. 20); searching from the first point P1 to outside, a point or region with most gray scale increase as the second point (as P2 shown in FIG. 20), and measuring the distance between the first point and the second points to characterize the width of posterior cranial fossa (CM). Certainly, searching from outside to center along the long axis may also get the same result. If it is a searching region, the gray scale of the region may be represented by mean value of gray scale of a plurality of pixels in the region, and performing the searching procedure of gray scale decrease or increase.

Step 423: marking the transverse diameter of the cerebellum (CTI) and/or posterior cranial fossawidth (CM) in the cerebellum section.

Specifically, automatically measure the lateral ventricle width (LV) on the lateral ventricle section. The lateral ventricle appears as low-echo region in ultrasonic image, and the peripheral tissue appears as non-low-echo. Take the fetal brain as an example, the positions of cerebellum and posterior cranial fossa of different fetus in the ellipse are approximately the same, thus may in a narrower scope, such as in the low-echo region of the ellipse, to segment the lateral ventricle according to characteristic of the lateral ventricle, after that, to select two ends of a width region as two ends of the LV. The step 183 to step 185 can be implemented as the following Step 431 to Step 433 respectively, and may include the following steps in detail:

Step 431: fitting the region of interest detected from the lateral ventricle section obtained according to aforementioned step S10-S20 by utilizing ellipse, and drawing an ellipse in the lateral ventricle section for characterizing the skull halo, by using aforementioned manner of Step 411.

According to a priori position, setting one searching region ROI or searching in the ellipse region, detecting upper and lower boundary of the lateral ventricle according to lateral ventricle boundary characteristic, obtaining the lateral ventricle boundary by using segmentation, marking and displaying the same; for example, the searching region ROI may be low-echo region in the image.

Step 432: measuring the distance of two end points with the widest vertical distance in the lateral ventricle region to characterize the width of the lateral ventricle (LV), which can be shown in FIG. 19.

Step 433: marking the width of the lateral ventricle (LV) in the lateral ventricle section.

Furthermore, it may automatically measure the posterior diameter of cauda cerebelli (CVAP), the uperoinferior diameter of cauda cerebelli (CVCC) and cauda cerebelli area (CVSA) on the median sagittal section.

The cauda cerebelli can be regarded as a joint of the upper cerebellum and the lower cerebellum in spatial. That is, it is located between the two cerebellums. Therefore, by automatic measurement of transverse diameter of the cerebellum according to Step 421 to Step 423, and the reference line of cerebellum section on the sagittal section, the X direction coordinate of the transverse diameter of the cerebellum corresponding on the sagittal section is just located on the cauda cerebelli. As the cauda cerebella appears brighter than peripheral tissue in ultrasonic image, so it may utilize this characteristic to select a priori ROI (region of interest) containing the cauda cerebelli. After that, it may segment the cauda cerebelli. Detailed methods of segment can be varies, such as region growing, automatic threshold segment, Graph Cut, Level Set and Snake, which will not be described in details herein. After the cauda cerebelli is segmented, the area of the cauda cerebelli (CVSA) can be calculated. The step 183 to step 185 may be implemented as the following Step 441 to Step 443 respectively, and may include the following steps in detail:

Step 441: designating a searching scope of the ROI of the cauda cerebelli, based on anatomical position of the cerebellum section marked on the median sagittal section and the transverse diameter of the cerebellum measured in the cerebellum section, by utilizing the characteristic that the cauda cerebella appears brighter than peripheral tissue in ultrasonic image, segmenting the ROI of the cauda cerebelli from the searching scope, and marking it to characterize the cauda cerebelli. If based on a gray scale image obtained by NMR and other equipment, the segmentation can be referenced to other image characteristic of the cauda cerebelli.

Step 442: calculating the area of the ROI of the cauda cerebelli to characterize the cauda cerebella area (CVSA).

Specifically, it may select two points with maximum distance along the horizontal direction and two points with maximum distance along the vertical distance in the ROI of the cauda cerebelli to calculate, respectively, the maximum distance of the horizontal direction and the maximum distance of the vertical direction, to respectively characterize the anteroposterior diameter and the uperoinferior diameter of the cauda cerebella. Or, it may perform fitting to the segmented ROI of the cauda cerebelli by utilizing an ellipse model, and measure the long axis and the short axis of the fitted ellipse to respectively characterize the anteroposterior diameter and the uperoinferior diameter of the cauda cerebella. The fitting method may be a least squares estimation method, etc.

Step 443: marking the cauda cerebella anteroposterior diameter (CVAP), the cauda cerebella uperoinferior diameter (CVCC) and/or the cauda cerebella area (CVSA) on the median sagittal section.

It should be noted that, the automatically measured items of related structure parameters provided by the aforementioned description of the present disclosure are just for convenience of expression, and should not be limited to the described order in practice. Furthermore, sub steps or stages are also not limited to the described orders.

In addition, in actual practice, for the automatically measured items of related structure parameters provided by the aforementioned description of the present disclosure, one or more items may be measured and displayed according to the user's need, or more items of the structure parameter with clinical sense may be added based on the disclosed system by utilizing similar methods. The adding or reducing of automatically measured items of related structure parameters are all belong to the scope of the present disclosure.

The aforementioned embodiments of the present disclosure may be used to calculate and display the 3D volume data corresponding to one moment/time, and also may be used to calculate and display a plurality of or a plurality of continuous 3D volume data. The present disclosure provides complete methods of automatically detecting encephalic standard sections and automatically measuring common used encephalic anatomical structure parameters. However, one or combination of more may also form an independent solution for solve a problem. For example, in aforementioned various embodiments, it may use a manner of combing the automatic detection and user input to make the obtaining and displaying of the image more accurate, and to make the user experience better. In addition, the detection of the related structure parameter may be a combination of automatic and user operation, which can fully satisfy clinical need and provide more flexible manner of operation.

In the aforementioned various embodiments, just the implementation manner of corresponding steps are described in detail, but in situation of no logical contradiction, the aforementioned embodiments may be combined to form one or more technical solutions, and these new technical solutions will be the disclosed scope of the detailed implementations of the present disclosure.

In the methods of the embodiments of the present disclosure, the automatic detection result of the sagittal section and/or the transverse section is substantially marking position of the sagittal section and/or transverse section in the 3D volume data coordinates, but the expression form may varies, for example, the plane equation, the amount of offsetting (amount of offsetting along the X, Y, Z direction) or amount of rotation (amount of rotation around the X, Y, Z axis) of the sagittal section or transverse section relative to the coordinate origin, the transformation matrix of the sagittal section or transverse section relative to the original coordinate (usually one 4×4 matrix can represent transformation relationship of two coordinates), or even the coordinate of three spatial points (three points can determine one plane), etc. Substantially, these expression forms/methods are marking the position of a plane in the 3D volume data coordinate, and can be converted between each other.

For the convenience of describing, in various embodiments the of the present disclosure, the expression form of plane equation is uniformly adopted. But the present disclosure is not limited to expression method of the plane equation, and the aforementioned expression methods or other methods in the art can also be included. Any expression form of the detection result of the sagittal section or transverse section is only different in expression form, thus should mot effect the substance of the present disclosure and should be the scope of the present disclosure.

Through the aforementioned embodiments, on skilled in the art can clearly understand that aforementioned methods of the embodiments may be implemented by hardware or by a processor executing software instructions stored in a memory. Based on these understanding, the technical solution of the present disclosure substantially can be implemented as a software product, or may say that the contribution part of the present disclosure to the related arts can be implemented as a software product. The software product can be loaded in a non-volatile computer-readable storage medium (such as ROM, magnetic disk, CD-ROM, storage space of a server), and may contain a plurality of instructions for making on terminal (may be a mobile phone, a computer, a server, or network equipment) to execute the steps of the methods described in embodiment of the present disclosure.

Based on one of the aforementioned embodiments of the present disclosure, the method may include the following steps:

Step 501, transmitting ultrasound to the head of the target body;

Step 502, receiving ultrasound echoes to obtain ultrasound echo signals;

Step 503, obtaining 3D volume data of the head of the target body according to the ultrasound echo signals;

Step 504, detecting, from the 3D volume data, a transverse section at an anatomical position according to image characteristic of the head of the target body in a transverse section related to the anatomical position;

Step 505, displaying the detected transverse section.

The detailed implementations of step 503 to step 505 can be referred to related description of step S10 to step S30, which will not be described herein again.

For another embodiment, based on one of the aforementioned embodiments of the present disclosure, it may include the following steps:

Step 601, transmitting ultrasound to the head of the target body;

Step 602, receiving ultrasound echoes to obtain ultrasound echo signals;

Step 603, obtaining 3D volume data of the head of the target body according to the ultrasound echo signals;

Step 604, detecting, from the 3D volume data, a section at an anatomical position according to image characteristic of the head of the target body in a section related to the anatomical position;

Step 605, marking the anatomical position corresponding to the detected section, and generating the indicator corresponding to the anatomical position;

Step 606, displaying the detected section and the indicator.

The detailed implementations of step 604 to step 606 can be referred to related description of step S91 to step S94, which will not be described herein again.

For another example, based on one of the aforementioned embodiments of the present disclosure, the method may include the following steps:

Step 701, transmitting ultrasound to the head of the target body;

Step 702, receiving ultrasound echoes to obtain ultrasound echo signals;

Step 703, obtaining 3D volume data of the head of the target body according to the ultrasound echo signals;

Step 704, detecting, from the 3D volume data, a section at an anatomical position according to image characteristic of the head of the target body in a section related to the anatomical position;

Step 705, detecting object of interest the of the section;

Step 706, measuring structure parameter of the object of interest;

Step 707, marking the object of interest and/or the structure parameter and displaying the same.

The detailed implementations of step 704 to step 707 can be referred to related description of step 182 to step 185, which will not be described herein again.

The 3D ultrasonic imaging method of aforementioned embodiments may be implemented in the 3D ultrasonic imaging system described by reference of FIG. 1. The 3D ultrasonic imaging system may include the probe 2, the 3D imaging unit 8 and the display 9. The probe 2 can transmit ultrasound to and receive ultrasound echoes from the head of the target body to obtain ultrasound echo signals. The 3D imaging unit 8 obtains the 3D volume data of the head of the target body such as the fetus head according to the ultrasound echo signals, by using a method according to any one of the aforementioned embodiments, to detect a median sagittal section image of the 3D volume data according to the user's selection or characteristics of the median sagittal section image of the head of the target body, and/or o detect a transverse section according to image characteristic of the head of the target body in a transverse section related to the anatomical position from the 3D volume data. The display 9 displays the detected median sagittal section image and/or the transverse section.

Or, in one embodiment of the present disclosure one, the 3D imaging unit 8 obtains the 3D volume data of the head of the target body such as the fetus head according to ultrasound echo signals, by using a method according to any one of the aforementioned embodiments, to detect a section at the anatomical position according to image characteristic of the head of the target body in a section related to the anatomical position from the 3D volume data, to mark an anatomical position corresponding to the detected section, and generate an indicator corresponding to the anatomical position. The display 9 displays the detected section and the indicator.

Or, in another embodiment of the present disclosure one, the 3D imaging unit 8 obtains the 3D volume data of the head of the target body such as the fetus head according to ultrasound echo signals, by using a method according to any one of the aforementioned embodiments, to detect a section at the anatomical position according to image characteristic of the head of the target body in a section related to the anatomical position from the 3D volume data, to detect object of interest of the section and measure structure parameters of the object of interest, and mark the aforementioned object of interest and/or the structure parameter. The display 9 displays the object of interest and/or the structure parameter.

In the embodiments of the present disclosure, the 3D ultrasonic imaging system may further include other elements, for example, the transmission/reception switch 3, the transmitting circuit 4, the receiving circuit 5, the beamformer unit 6, and the signal processing unit 7 as shown in FIG. 1. These elements will not be described in details again.

According to various embodiments of the present disclosure, the 3D ultrasonic imaging system for implementing the aforementioned embodiments is not limited to common integrated ultrasonic imaging system (for example, a car type ultrasonic imaging system or a portable ultrasonic imaging system). It may also be a distributed system, for example, at least partial step or function of the methods according to aforementioned embodiments (for example, the step of detecting median sagittal section image from the 3D volume data) may be implemented in other equipment (for example, a data processing workstation, a personal computer, various kinds of intelligent portable equipment, other ultrasonic imaging equipment, or various kinds of web server) connected to the car type ultrasonic imaging system or the portable ultrasonic imaging system via the data communication device (wired or wireless), thus the other equipment and the car type ultrasonic imaging system or the portable ultrasonic imaging system corporately form the 3D ultrasonic imaging system of the embodiments according to the present disclosure.

By practicing of the methods of the present disclosure, the system can automatically display sections such as fetus median sagittal section, cerebellum section, thalamus section, and lateral ventricle section, and may further automatically measure anatomical structure of the sections, which may save the examination time and greatly decrease the dependence to the technical level of the doctor.

The ultrasonic imaging method according to the embodiments of the present disclosure may obtain fetus head 3D volume data by performing ultrasonic scan to fetus, and automatically detect and display the median sagittal section image of the fetal brain according to the obtained 3D volume data, which may solve the problem that it's hard for the doctor to manually and accurately localize the median sagittal section image, and allow the doctor to conveniently observe the situation of the fetal brain median sagittal section image and provide a great amount of important key information to the practitioner.

The present disclosure specifically provides a method and system for automatically identifying fetus encephalic standard section from 3D or 4D fetus volume data, the obtained standard section includes fetus median sagittal section, cerebellum section, thalamus section, and lateral ventricle section. After finishing the collection of the 3D\4D data, it only needs to press one button or menu, and then the system can automatically display the fetus median sagittal section, the cerebellum section, the thalamus section, and the lateral ventricle section. Meanwhile, it also can automatically measure indicators including the biparietal diameter, the occipito-frontal diameter, the head circumference, the transverse diameter of the cerebellum, the posterior cranial fossa width, the lateral ventricle width, the cauda cerebelli transverse diameter and longitudinal diameter, and the cauda cerebella area, which may greatly decrease the dependence to the technical level of the doctor, thus to save the examination time.

The embodiments of the ultrasonic imaging method according to the present disclosure may perform ultrasonic scan to the head of a target body such as a fetus, thus to obtain 3D volume data of the head of the target body, automatically detect the transverse section image of the brain of the target body at a specific anatomical position according to the obtained 3D volume data, and display the transverse section image. Furthermore, the present disclosure may apply the display analysis processing procedure of the 3D volume data to all kinds of 3D volume data, and should not be limited to 3D volume data obtained through ultrasound. Furthermore, the methods of the present disclosure may perform segment of region of interest and parameter calculation based on the automatically detected section images such as the transverse section image and the sagittal section image, and display the same. Furthermore, the present disclosure may mark and display the sectioning positions based on the automatically detected section images such as the transverse section image and the sagittal section image. The present disclosure may solve the problem that manual operation of the doctor is hard to correctly localize a transverse section image at a specific anatomical position, therefore the doctor may conveniently observe situations of the transverse section image of the fetal brain, and may provide practitioners a great amount of important key information. Furthermore, it may provide the doctor more accurately localized section images, and regions of interest in the image and related parameter information, and additionally provides the doctor more friendly display and operation manner.

In addition, the present disclosure provides a method and system of automatically identifying the encephalic standard section image of fetus from 3D/4D fetus volume data, the obtained standard section images include fetus median sagittal section image, cerebellum section image, thalamus section image and lateral ventricle section image. The system can automatically display the fetus median sagittal section image, the cerebellum section image, the thalamus section image and the lateral ventricle section image after the doctor finished the 3D/4D data collection. At the same time, it may automatically measure the indicators such as the biparietal diameter, the occipito-frontal diameter, the head circumference, the transverse diameter of cerebellum, the width of posterior cranial fossa, the lateral ventricle width, the cauda cerebelli transverse diameter, the longitudinal diameter and the cauda cerebelli area, therefore may significantly reduce dependence on the technical level of the doctor, thus to save the examination time.

The foregoing embodiments with detailed descriptions represent several implementations of the present disclosure, but they should not be construed as limiting the scope of the present disclosure. It should be understood that, for those skilled in the art, a number of modifications and improvements can also be made without departing from the idea of the present disclosure, which is within the claimed scope of the present disclosure. In addition, the phrase of "one embodiment" may represent different embodiments, and all embodiments or a part of them can be combined in one embodiment.

What is claimed is:

1. A method for processing 3D image data, comprising:
   obtaining, by an ultrasonic imaging system, 3D volume data of a head of a target body;
   obtaining, by the ultrasonic imaging system, an image characteristic corresponding to a specified transverse section at an anatomical position of a fetal head from a transverse section template image, the transverse section template image being previously generated for a sample body, the image characteristic comprising at least one of a shape characteristic, a textural characteristic, and a spatial relationship characteristic, the shape characteristic being obtained from the transverse section template image using one of a Hough transformation and a boundary direction histogram, the textural characteristic being obtained from the transverse section template image using at least one of an energy spectrum function, a grayscale co-occurrence matrix, and a random field model, and the spatial relationship characteristic being obtained from the transverse section template image based on a mutual spatial position or relative direction relationship between a plurality of targets segmented from the transverse section template image, wherein the specified transverse section includes at least one of a cerebellum section and a thalamus section and a lateral ventricle section;

detecting, by a processor of the ultrasonic imaging system, a location of a cavum septi pellucidi in the 3D volume data of the head of the target body;

extracting, by the processor of the ultrasonic imaging system, a candidate transverse section image set comprising candidate traverse section images that pass through the location of the cavum septi pellucidi from the obtained 3D volume data;

automatically identifying, by the processor of the ultrasonic imaging system, a target transverse section image from the candidate transverse section image set that comprises the image characteristic corresponding to the specified transverse section at the anatomical position from the candidate transverse section images of the candidate transverse section image set that pass through the location of the cavum septi pellucidi; and displaying the target transverse section image.

2. The method of claim 1, wherein determining the target transverse section image that comprises the image characteristic corresponding to the specified transverse section at the anatomical position from the candidate transverse section images of the candidate transverse section image set that pass through the location of the cavum septi pellucidi comprises:

calculating a similarity index between each candidate transverse section image of the candidate transverse section image set and the transverse section template image to obtain a set of similarity indexes;

selecting a similarity index which satisfies an image characteristic condition from the set of similarity indexes; and obtaining the candidate transverse section image corresponding to the selected similarity index as the target transverse section image.

3. A method for 3D ultrasonic imaging of an ultrasonic imaging system, comprising:

transmitting, by an ultrasonic probe of the ultrasonic imaging system, ultrasound waves to a head of a target body;

receiving, by the ultrasonic probe, ultrasonic echoes to obtain ultrasonic echo signals;

obtaining, by a processor of the ultrasonic imaging system, 3D volume data of the head of the target body based on the ultrasonic echo signals;

obtaining, by the ultrasonic imaging system, an image characteristic corresponding to a specified transverse section at an anatomical position of a fetal head from a transverse section template image, the transverse section template image being previously generated for a sample body, the image characteristic comprising at least one of a shape characteristic, a textural characteristic, and a spatial relationship characteristic, the shape characteristic being obtained from the transverse section template image using one of a Hough transformation and a boundary direction histogram, the textural characteristic being obtained from the transverse section template image using at least one of an energy spectrum function, a grayscale co-occurrence matrix, and a random field model, and the spatial relationship characteristic being obtained from the transverse section template image based on a mutual spatial position or relative direction relationship between a plurality of targets segmented from the transverse section template image, wherein the specified transverse section includes at least one of a cerebellum section, a thalamus section and a lateral ventricle section;

detecting, by a processor of the ultrasonic imaging system, a location of a cavum septi pellucidi in the 3D volume data of the head of the target body;

extracting, by the processor of the ultrasonic imaging system, a candidate transverse section image set comprising candidate transverse section images that pass through the location of the cavum septi pellucidi from the obtained 3D volume data;

automatically identifying, by the processor of the ultrasonic imaging system, a target transverse section image from the candidate traverse section image set that comprises the image characteristic corresponding to the specified transverse section at the anatomical position from the candidate transverse section images of the candidate transverse section image set that pass through the location of the cavum septi pellucidi; and displaying the target transverse section image.

4. The method of claim 3, wherein determining a target transverse section image that comprises the image characteristic corresponding to the specified transverse section at the anatomical position from the candidate transverse section images of the candidate transverse section image set that pass through the location of the cavum septi pellucidi comprises:

calculating a similarity index between each candidate transverse section image of the candidate transverse section image set and the transverse section template image to obtain a set of similarity indexes;

selecting a similarity index which satisfies an image characteristic condition from the set of similarity indexes; and obtaining the candidate transverse section image corresponding to the selected similarity index as the target transverse section image.

5. A 3D ultrasonic imaging system, comprising:

a probe which transmits ultrasound to and receives ultrasound echoes from a head of a target body to obtain ultrasound echo signals;

a processor which:

obtains 3D volume data based on the ultrasound echo signals;

obtains an image characteristic corresponding to a specified transverse section at an anatomical position of a fetal head from a transverse section template image, the transverse section template image being previously generated for a sample body, the image characteristic comprising at least one of a shape characteristic, a textural characteristic, and a spatial relationship characteristic, the shape characteristic being obtained from the transverse section template image using one of a Hough transformation and a boundary direction histogram, the textural characteristic being obtained from the transverse section template image using at least one of an energy spectrum function, a grayscale co-occurrence matrix, and a random field model, and the spatial relationship characteristic being obtained from the transverse section template image based on a mutual spatial position or relative direction relationship between a plurality of targets segmented from the transverse section template image, wherein the specified transverse section includes at least one of a cerebellum section, a thalamus section and a lateral ventricle section;

detects a location of a cavum septi pellucidi in the 3D volume data of the head of the target body;

extracts a candidate transverse section images set comprising candidate traverse section images that pass through the location of the cavum septi pellucidi from the obtained 3D volume data; and automatically identifies a target transverse section image from the candidate transverse section image set that comprises the image characteristic corresponding to the specified transverse section at the anatomical position from the candidate transverse section images of the candidate transverse section image set that pass through the location of the cavum septi pellucidi; and a display which displays the target transverse section image.

6. The method of claim 1, wherein the image characteristic comprises one or more of a color characteristic and a projection characteristic of the image.

7. The method of claim 1, wherein the transverse section template image includes at least one standard transverse section image, or includes at least one standard transverse section image and at least one non-standard transverse section image.

8. The method of claim 7, wherein the standard transverse section image is obtained from the anatomical position of at least one sample body, and the non-standard transverse section image is obtained from at least one position deviated from the anatomical position of at least one sample body.

9. The method of claim 2, wherein calculating the similarity index between each candidate transverse section image of the candidate transverse section image set and the transverse section template image to obtain the set of similarity indexes comprises:

extracting an image characteristic from the transverse section template image to obtain a first characteristic;

respectively extracting an image characteristic from each candidate transverse section image of the candidate transverse section image set as a second characteristic to obtain a set of second characteristics; and respectively calculating a likelihood between each second characteristic of the set of second characteristics and the first characteristic to obtain the set of similarity indexes.

10. The method of claim 2, wherein calculating the similarity index between each candidate transverse section image of the candidate transverse section image set and the transverse section template image to obtain the set of similarity indexes comprises:

constructing an image classification model, and training the image classification model by utilizing the transverse section template image to obtain a trained image classification model; and respectively inputting each candidate transverse section image of the candidate transverse section image set to the trained image classification model to obtain a classification tag corresponding to each candidate transverse section image to obtain the set of similarity indexes.

11. The method of claim 2, wherein prior to calculating the similarity index between each candidate transverse section image of the candidate transverse section image set and the transverse section template image to obtain the set of similarity indexes, the method further comprises:

adjusting the candidate transverse section image set and/or the transverse section template image such that the candidate transverse section image set and the transverse section template image have a same scale.

* * * * *